United States Patent
Smith

(10) Patent No.: US 10,010,623 B2
(45) Date of Patent: *Jul. 3, 2018

(54) LYSOSOME-CLEAVABLE LINKER

(71) Applicant: UCL Business PLC, London (GB)

(72) Inventor: Mark Edward Brennan Smith, London (GB)

(73) Assignee: UCL Business PLC (GB)

( * ) Notice: Subject to any disclaimer, the term of this patent is extended or adjusted under 35 U.S.C. 154(b) by 185 days.

This patent is subject to a terminal disclaimer.

(21) Appl. No.: 14/378,138

(22) PCT Filed: Feb. 5, 2013

(86) PCT No.: PCT/GB2013/050258
§ 371 (c)(1),
(2) Date: Aug. 12, 2014

(87) PCT Pub. No.: WO2013/121175
PCT Pub. Date: Aug. 22, 2013

(65) Prior Publication Data
US 2015/0037360 A1 Feb. 5, 2015

Related U.S. Application Data

(60) Provisional application No. 61/599,451, filed on Feb. 16, 2012.

(51) Int. Cl.
| | |
|---|---|
| *A61K 47/68* | (2017.01) |
| *A61K 31/537* | (2006.01) |
| *A61K 47/48* | (2006.01) |
| *A61K 31/704* | (2006.01) |
| *C07D 207/24* | (2006.01) |
| *C07H 15/26* | (2006.01) |
| *C07K 16/18* | (2006.01) |
| *A61K 39/00* | (2006.01) |

(52) U.S. Cl.
CPC ...... *A61K 47/48384* (2013.01); *A61K 31/704* (2013.01); *A61K 47/48407* (2013.01); *A61K 47/48576* (2013.01); *A61K 47/48584* (2013.01); *A61K 47/48715* (2013.01); *C07D 207/24* (2013.01); *C07H 15/26* (2013.01); *C07K 16/18* (2013.01); *A61K 2039/505* (2013.01); *C07K 2317/24* (2013.01); *C07K 2317/50* (2013.01)

(58) Field of Classification Search
None
See application file for complete search history.

(56) References Cited

U.S. PATENT DOCUMENTS

| | | | |
|---|---|---|---|
| 2,859,243 A | 11/1958 | Reed | |
| 2004/0092578 A1 | 5/2004 | Sheppard et al. | |
| 2006/0122096 A1 | 6/2006 | Rozema et al. | |
| 2009/0074885 A1 | 3/2009 | Monahan et al. | |
| 2013/0224228 A1 | 8/2013 | Jackson et al. | |

FOREIGN PATENT DOCUMENTS

| | | |
|---|---|---|
| WO | 2011-018611 A1 | 2/2011 |
| WO | 2011-018612 A2 | 2/2011 |
| WO | 2011-018613 A1 | 2/2011 |

OTHER PUBLICATIONS

Doronina et al. ("Doronina", BioconjugateChem., 2006, 17, 114-124).*
Smith et al. ("Smith", J. Am. Chem. Soc., 2010, 132, 1960-1965).*
Lyon et al Nature Biotech 2014, 32, 1059-1062.*
Chris P. Ryan et al., "Tunable reagents for multi-functional bioconjugation: reversible or permanent chemical modification of proteins and peptides by control of maleimide hydrolysis", Chem. Commun., Apr. 5, 2011, 47, 5452-5454.
Blättler et al., "New heterobifunctional protein cross-linking reagent that forms an acid labile link", Biochemistry 1985, 24:15, 17-24.
Haas et al., "Targeting of doxorubicin to the urinary bladder of the rat shows increased cytotoxicity in the bladder urine with an absence of renal toxicity", Journal of Drug Targeting, 2002, 10: 81-89.
Dyba et al., "Small Molecule Toxins Targeting Tumor Receptors", Current Pharmaceutical Design, 2004, 10(19), 2311-2334.
Kirby et al., "Structure and efficiency in intramolecular and enzymic catalysis. Catalysis of amide hydrolysis by the carboxy-group of substituted maleamic acids", J. Chem. Soc., Perkin Trans. 1972, 2, 1206-1214.
Glusenkamp et al., "Rapid hydrolysis of amides under physiological conditions: influence of the microenvironment on the stability of the amide bond", Bioorg Med Chem Lett., 1998, 8(3), 285-8.
Rozema et al., "Endosomolysis by Masking of a Membrane-Active Agent (EMMA) for Cytoplasmic Release of Macromolecules", Bioconjugate Chem., 2003, 14, 51-57.
Rozema et al., "Dynamic PolyConjugates for targeted in vivo delivery of siRNA to hepatocytes", Proc. Natl. Acad. Sci. USA, 2007, 104, 12982-12987.
Muldoon et al., "BR96-DOX immunoconjugate targeting of chemotherapy in brain tumour models", Journal of Neuro-Oncology, 2003, 65, 49-62.
Hudecz et al., "Immunoconjugate Design: A Predictive Approach for Coupling of Daunomycin to Monoclonal Antibodies", Bioconjugate Chem., 1990, 1, 197-204.
International Search Report, International Searching Authority, PCT No. GB2013/050258, International Filing Date Feb. 5, 2013.

* cited by examiner

*Primary Examiner* — Mark Halvorson
*Assistant Examiner* — Kauser M Akhoon
(74) *Attorney, Agent, or Firm* — Dorf & Nelson LLP; Scott D. Locke, Esq.

(57) ABSTRACT

The present invention relates to a linker for forming conjugates of a protein or peptide with a therapeutically active agent and which comprise a thiomaleamic acid moiety that is susceptible to cleavage under the pH conditions prevalent in the lysosome.

24 Claims, 3 Drawing Sheets

LYSOSOME-CLEAVABLE LINKER

This application is a National Stage Application of PCT/GB2013/050258, international filing date Feb. 5, 2013, which claim priority to U.S. Provisional Patent Application Ser. No. 61/599,451, filed on Feb. 16, 2012; the present application claims priority to the afore-referenced applications and those applications are incorporated herein by reference.

The invention relates to conjugates comprising a protein or peptide and a therapeutically active agent connected via a thiomaleamic acid linker that is susceptible to hydrolysis under lysosomal conditions.

BACKGROUND

Antibody-drug-conjugates (ADCs) combine the power of antibody selectivity with the therapeutic activity of small drugs.

Interest in this rapidly growing field has focussed primarily on ADCs for use in cancer therapy. In such conjugates, an antibody is selected typically to target a cell surface receptor that is over-expressed on the surface of cancer cells. After the specific antibody-antigen interaction has occurred at the cancer cell, the ADC becomes internalised and subsequently processed through endosomes and then lysosomes within the cell.

It is generally necessary for an ADC to fragment and thereby to release the drug in order to achieve a therapeutic effect. Typically, this has been accomplished through the use of labile linkers connecting, or "conjugating", the drug to the antibody. It is important that the linker retains its structural integrity until the ADC has been successfully delivered to the target cell, but then cleaves to release the drug cargo once the ADC has been localised.

Many linkers currently favoured in the art derive their lability through their susceptibility to cleavage by the protease enzymes that exist within the lysosome. However, proteases are also present in significant quantities in blood serum. Unfortunately, this can lead to premature release of the drug cargo when an ADC is administered systemically. This in turn can generate potentially serious side effects, particularly in view of the fact that the drug part of an anti-cancer ADC is typically a cytotoxin.

Consequently, there is a need in the art for further linkers that do not cleave prematurely, for example in blood serum following administration of an ADC, but which still cleave efficiently to release a drug cargo once an ADC has been delivered to a target cell.

This patent application describes bioconjugates that are connected via a specifically designed thiomaleamic acid linker moiety that is stable under physiological conditions such as those characterising blood serum, but which undergoes efficient acid-catalysed cleavage under pH conditions directly aligned with those existing within the lysosome.

SUMMARY

The present inventors have identified a particular type of linker that is susceptible to acid-catalysed cleavage at a pH of from 4 to 5, which aligns ideally with the pH environment within the lysosome. The linker is not susceptible to cleavage at higher pHs such as those characterising blood serum. Furthermore, the linker does not derive its lability from protease-catalysed cleavage, meaning that there is no danger of undesirable protease-catalysed drug release in blood serum. Consequently, conjugates comprising the new linker are ideally suited for therapeutic applications that involve cell-specific targeting and release of a drug cargo within the targeted cell.

Thus, the present invention provides compound comprising a moiety of formula (I) or (I')

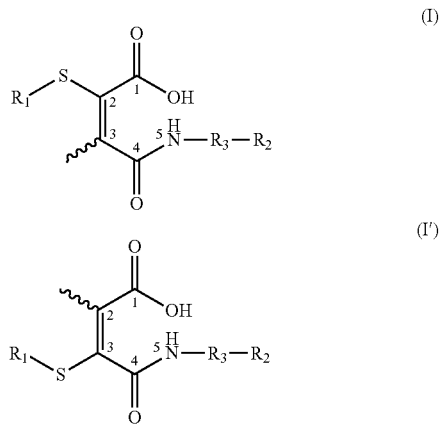

wherein:
$R_1$ is a protein or peptide;
$R_2$ is a therapeutically active agent; and
$R_3$ is a linker moiety or a bond;
$R_1$ being linked to the 2-position of the moiety of formula (I) via a first sulfur atom attached to the 2-position of the moiety of formula (I); and $R_1$ being linked to the 3-position of the moiety of formula (I') via a first sulfur atom attached to the 3-position of the moiety of formula (I').

The present invention also provides a pharmaceutical composition comprising: (i) a compound comprising a moiety of formula (I) or (I'); and (ii) a pharmaceutically acceptable diluent or carrier.

The present invention further provides a method of ameliorating or reducing the incidence of cancer in a subject, which method comprises the administration to the said subject of an effective amount of a compound comprising a moiety of formula (I) or (I') and wherein $R_1$ is an antibody or antibody fragment that is capable of specific binding to a cancer cell and $R_2$ is a cytotoxic agent.

The present invention still further provides a compound comprising a moiety of formula (I) or (I') for use in a method of treatment of the human or animal body by therapy.

The present invention also provides a compound comprising a moiety of formula (I) or (I') for use in a method of treatment of cancer, wherein $R_1$ is an antibody or antibody fragment that is capable of specific binding to a cancer cell and $R_2$ is a cytotoxic agent.

Further preferred features and embodiments are described in the accompanying description and the appended claims.

DETAILED DESCRIPTION

Figure 1:
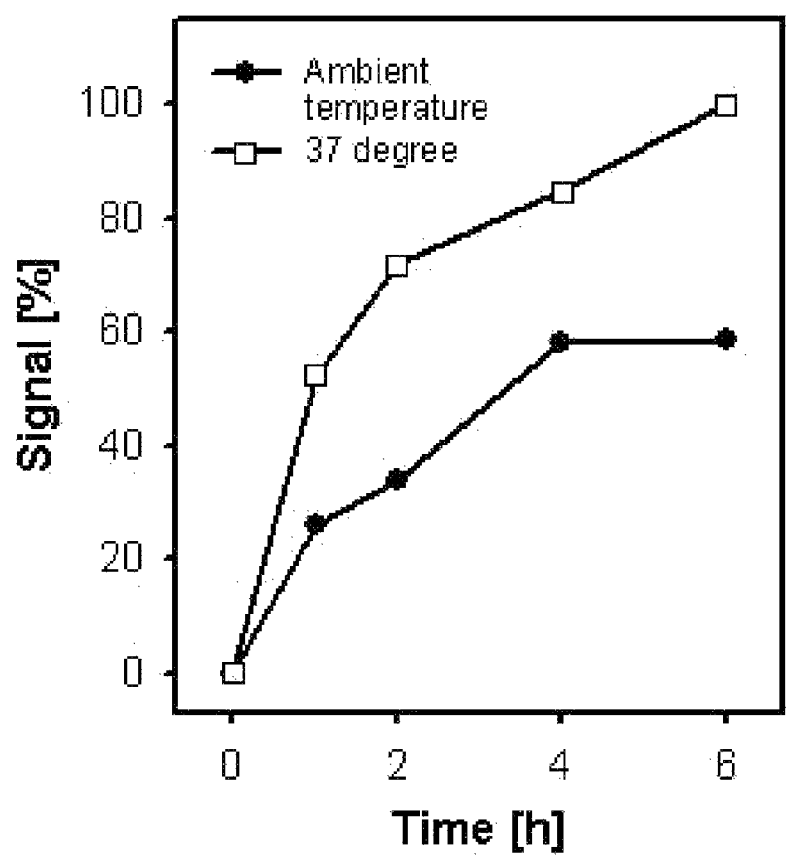
FIG. 1 depicts the results of time-dependent LCMS analysis of the hydrolysis of a modified antibody compound as described in Example 1. The x-axis represents time in hours and the y-axis represents the LCMS signal as a percentage of signal corresponding to complete hydrolysis. Open squares correspond to results obtained at 37° C. and filled diamonds correspond to results obtained at ambient temperature.

As used herein, an "antibody" includes monoclonal antibodies, polyclonal antibodies, monospecific antibodies and multispecific antibodies (e.g., bispecific antibodies). An "antibody fragment" is a fragment of such an antibody that exhibits the desired biological activity, e.g. the activity or substantially the activity of its corresponding "intact" antibody.

Antibodies (and antibody fragments) as used herein includes fusion proteins of antibodies (and antibody fragments) where a protein is fused via a covalent bond to the antibody (or antibody fragment). Also included are chemical analogues and derivatives of antibodies and antibody fragments, provided that the antibody or antibody fragment maintains its ability to bind specifically to its target antigen. Thus, for example, chemical modifications are possible (e.g., glycosylation, acetylation, PEGylation and other modifications without limitation) provided specific binding ability is retained.

An antibody comprises a variable region, which is capable of specific binding to a target antigen, and a constant region. An antibody as defined herein can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

As used herein a "monoclonal antibody" is an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site.

"Monoclonal antibodies" as defined herein may be chimeric antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

An "intact antibody" is one that comprises an antigen-binding variable region as well as a light chain constant domain (CL) and heavy chain constant domains, CH1, CH2, CR3 and CH4, as appropriate for the antibody class. The constant domains may be native sequence constant domains such as human native sequence constant domains or amino acid sequence variants thereof.

An intact antibody may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immunospecifically bind to a target antigen (e.g., a cancer cell antigen).

"Humanized" forms of non-human (e.g., rodent) antibodies are chimeric antibodies that contain minimal sequence derived from non-human immunoglobulin.

The term "capable of specific binding" refers to protein or peptide (e.g., antibody) binding to a predetermined target substance (e.g., an antigen and/or groups of antigens), e.g. a target substance that is expressed on the surface of a cell; thus the term "binding to a target cell" or "binding to a cancer cell" is to be understand as referring to protein or peptide (e.g., antibody) binding to a predetermined target substance (e.g. antigen or antigens) that is expressed on such a cell.

Typically, the protein or peptide (e.g., antibody) binds with an affinity of at least about $1 \times 10^7$ M$^{-1}$, and/or binds to the predetermined target substance (e.g., antigen, antigens or cell) with an affinity that is at least two-fold greater than its affinity for binding to a non-specific control substance (e.g., BSA, casein, non-cancer cells) other than the predetermined target substance or a closely-related target substance.

As used herein, the term "alkyl" includes both saturated straight chain and branched alkyl groups. Preferably, an alkyl group is a $C_{1-20}$ alkyl group, more preferably a $C_{1-15}$, more preferably still a $C_{1-12}$ alkyl group, more preferably still, a $C_{1-6}$ alkyl group, and most preferably a $C_{1-4}$ alkyl group. Particularly preferred alkyl groups include, for example, methyl, ethyl, propyl, isopropyl, butyl, isobutyl, tert-butyl, pentyl and hexyl. The term "alkylene" should be construed accordingly.

As used herein, the term "alkenyl" refers to a group containing one or more carbon-carbon double bonds, which may be branched or unbranched. Preferably the alkenyl group is a $C_{2-20}$ alkenyl group, more preferably a $C_{2-15}$ alkenyl group, more preferably still a $C_{2-12}$ alkenyl group, or preferably a $C_{2-6}$ alkenyl group, and most preferably a $C_{2-4}$ alkenyl group. The term "alkenylene" should be construed accordingly.

As used herein, the term "alkynyl" refers to a carbon chain containing one or more triple bonds, which may be branched or unbranched. Preferably the alkynyl group is a $C_{2-20}$ alkynyl group, more preferably a $C_{2-15}$ alkynyl group, more preferably still a $C_{2-12}$ alkynyl group, or preferably a $C_{2-6}$ alkynyl group and most preferably a $C_{2-4}$ alkynyl group. The term "alkynylene" should be construed accordingly.

Unless otherwise specified, an alkyl, alkenyl or alkynyl group is typically unsubstituted. However, where such a group is indicated to be unsubstituted or substituted, one or more hydrogen atoms are optionally replaced by halogen atoms or sulfonic acid groups. Preferably, a substituted alkyl, alkenyl or alkynyl group has from 1 to 10 substituents, more preferably 1 to 5 substituents, more preferably still 1, 2 or 3 substituents and most preferably 1 or 2 substituents, for example 1 substituent. Preferably a substituted alkyl, alkenyl or alkynyl group carries not more than 2 sulfonic acid substituents. Halogen atoms are preferred substituents. Preferably, though, an alkyl, alkenyl or alkynyl group is unsubstituted.

In the moiety that is an alkyl, alkenyl or alkynyl group in which (a) 0, 1 or 2 carbon atoms may be replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups may be replaced by groups selected from —O—, —S—, —S—S—, —C(O)— and —N($C_{1-6}$ alkyl)- groups, a total of 0, 1 or 2 of said carbon atoms and —$CH_2$— groups are preferably replaced, more preferably a total of 0 or 1. Most preferably, none of the carbon atoms or —$CH_2$— groups is replaced.

In the moiety that is an alkylene, alkenylene or alkynylene group, in which (a) 0, 1 or 2 carbon atoms may be replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups may be replaced by groups selected from —O—, —S—, —S—S—, —C(O)—, —N(H)—, —N($C_{1-6}$ alkyl)-, —O—C(O)—, O—C(O)—NH—, —NH—C(O)— and —NH—C(O)—O groups, preferably at least one carbon atom is replaced. Preferred groups for replacing a carbon atom are phenylene, 5- to 6-membered heteroarylene, $C_{5-6}$ carbocyclylene and 5- to 6-membered heterocyclylene groups. Preferably at least one —$CH_2$— group is replaced, preferably by a group selected from —O—C(O)—, O—C(O)—NH—, —NH—C(O)— and —NH—C(O)—O. Preferably a total of 0, 1, 2 or 3 of said carbon atoms and —$CH_2$— groups are preferably replaced, more preferably a total of 2 or 3. Particularly preferably, at least one carbon atom is replaced and at least one —$CH_2$— group is replaced by a group selected from —O—C(O)—, O—C(O)—NH—, —NH—C(O)— and —NH—C(O)—O (most preferably the said carbon atom being adjacent to the nitrogen at the 5-position of the moiety of formula (I) and the said —$CH_2$— group being adjacent to $R_2$).

As used herein, the reference to "0, 1 or 2 carbon atoms" means any terminal or non-terminal carbon atom in the alkyl, alkenyl or alkynyl chain, or alkylene, alkenylene or alkynylene chain, including any hydrogen atoms attached to that carbon atom. As used herein, the reference to "0, 1 or 2 —$CH_2$— groups" refers to a group which does not correspond to a terminal carbon atom in the alkyl, alkenyl or alkynyl chain (but may correspond to a terminal carbon atom in the alkylene, alkenylene or alkynylene chain).

As used herein, a $C_{6-10}$ aryl group is a monocyclic or polycyclic 6- to 10-membered aromatic hydrocarbon ring system having from 6 to 10 carbon atoms. Phenyl is preferred. The term "arylene" should be construed accordingly. Thus, a preferred arylene group is a phenylene group.

As used herein, a 5- to 10-membered heteroaryl group is a monocyclic or polycyclic 5- to 10-membered aromatic ring system, such as a 5- or 6-membered ring, containing at least one heteroatom, for example 1, 2, 3 or 4 heteroatoms, selected from O, S and N. When the ring contains 4 heteroatoms these are preferably all nitrogen atoms. The term "heteroarylene" should be construed accordingly.

Examples of monocyclic heteroaryl groups include thienyl, furyl, pyrrolyl, imidazolyl, thiazolyl, isothiazolyl, pyrazolyl, oxazolyl, isoxazolyl, triazolyl, thiadiazolyl, oxadiazolyl, pyridinyl, pyridazinyl, pyrimidinyl, pyrazinyl, triazinyl and tetrazolyl groups.

Examples of polycyclic heteroaryl groups include benzothienyl, benzofuryl, benzimidazolyl, benzothiazolyl, benzisothiazolyl, benzoxazolyl, benzisoxazolyl, benztriazolyl, indolyl, isoindolyl and indazolyl groups. Preferred polycyclic groups include indolyl, isoindolyl, benzimidazolyl, indazolyl, benzofuryl, benzothienyl, benzoxazolyl, benzisoxazolyl, benzothiazolyl and benzisothiazolyl groups, more preferably benzimidazolyl, benzoxazolyl and benzothiazolyl, most preferably benzothiazolyl. However, monocyclic heteroaryl groups are preferred.

Preferably the heteroaryl group is a 5- to 6-membered heteroaryl group. Particularly preferred heteroaryl groups are thienyl, pyrrolyl, imidazolyl, thiazolyl, isothiazolyl, pyrazolyl, oxazolyl, isoxazolyl, triazolyl, pyridinyl, pyridazinyl, pyrimidinyl and pyrazinyl groups. More preferred groups are thienyl, pyridinyl, pyridazinyl, pyrimidinyl, pyrazinyl, pyrrolyl and triazinyl, most preferably pyridinyl.

As used herein, a 5- to 10-membered heterocyclyl group is a non-aromatic, saturated or unsaturated, monocyclic or polycyclic $C_{5-10}$ carbocyclic ring system in which one or more, for example 1, 2, 3 or 4, of the carbon atoms are replaced with a moiety selected from N, O, S, S(O) and $S(O)_2$. Preferably, the 5- to 10-membered heterocyclyl group is a 5- to 6-membered ring. The term "heterocyclyene" should be construed accordingly.

Examples of heterocyclyl groups include azetidinyl, oxetanyl, thietanyl, pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, methylenedioxyphenyl, ethylenedioxyphenyl, thiomorpholinyl, S-oxothiomorpholinyl, S,S-dioxo-thiomorpholinyl, morpholinyl, 1,3-dioxolanyl, 1,4-dioxolanyl, trioxolanyl, trithianyl, imidazolinyl, pyranyl, pyrazolinyl, thioxolanyl, thioxothiazolidinyl, 1H-pyrazol-5-(4H)-onyl, 1,3,4-thiadiazol-2(3H)-thionyl, oxopyrrolidinyl, oxothiazolidinyl, oxopyrazolidinyl, succinimido and maleimido groups and moieties. Preferred heterocyclyl groups are pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, thiomorpholinyl and morpholinyl groups and moieties. More preferred heterocyclyl groups are tetrahydropyranyl, tetrahydrothiopyranyl, thiomorpholinyl, tetrahydrofuranyl, tetrahydrothienyl, piperidinyl, morpholinyl and pyrrolidinyl groups.

For the avoidance of doubt, although the above definitions of heteroaryl and heterocyclyl groups refer to an "N" moiety which can be present in the ring, as will be evident to a skilled chemist the N atom will be protonated (or will carry a substituent as defined below) if it is attached to each of the adjacent ring atoms via a single bond.

As used herein, a $C_{3-7}$ carbocyclyl group is a non-aromatic saturated or unsaturated hydrocarbon ring having from 3 to 7 carbon atoms. Preferably it is a saturated or mono-unsaturated hydrocarbon ring (i.e. a cycloalkyl moiety or a cycloalkenyl moiety) having from 3 to 7 carbon atoms, more preferably having from 5 to 6 carbon atoms. Examples include cyclopropyl, cyclobutyl, cyclopentyl and cyclohexyl and their mono-unsaturated variants. Particularly preferred carbocyclic groups are cyclopentyl and cyclohexyl. The term "carbocyclylene" should be construed accordingly.

Where specified, 0, 1 or 2 carbon atoms in a carbocyclyl or heterocyclyl group may be replaced by —C(O)— groups. As used herein, the "carbon atoms" being replaced are understood to include the hydrogen atoms to which they are attached. When 1 or 2 carbon atoms are replaced, preferably two such carbon atoms are replaced. Preferred such carbocyclyl groups include a benzoquinone group and preferred such heterocyclyl groups include succinimido and maleimido groups.

Unless otherwise specified, an aryl, heteroaryl, carbocyclyl or heterocyclyl group is typically unsubstituted. However, where such a group is indicated to be unsubstituted or substituted, one or more hydrogen atoms are optionally replaced by halogen atoms or $C_{1-6}$ alkyl, $C_{1-6}$ alkoxy, $C_{1-6}$ alkylthiol, —N($C_{1-6}$ alkyl)($C_{1-6}$ alkyl), nitro or sulfonic acid groups. Preferably, a substituted aryl, heteroaryl, carbocyclyl or heterocyclyl group has from 1 to 4 substituents, more preferably 1 to 2 substituents and most preferably 1 substituent. Preferably a substituted aryl, heteroaryl, carbocyclyl or heterocyclyl group carries not more than 2 nitro substituents and not more than 2 sulfonic acid substituents. Preferred substituents are halogen atoms and $C_{1-4}$ alkyl and $C_{1-4}$ alkoxy groups. Particularly preferred substituents are halogen atoms. Preferably, though, an aryl, heteroaryl, carbocyclyl or heterocyclyl group is unsubstituted.

As used herein, halogen atoms are typically F, Cl, Br or I atoms, preferably Br or Cl atoms, more preferably Br atoms.

As used herein, a $C_{1-6}$ alkoxy group is a $C_{1-6}$ alkyl (e.g. a $C_{1-4}$ alkyl) group which is attached to an oxygen atom.

As used herein, a $C_{1-6}$ alkylthiol group is a $C_{1-6}$ alkyl (e.g. a $C_{1-4}$ alkyl) group which is attached to a sulfur atom.

As used herein, the symbol ∿ means a point of attachment to another chemical group. The specific chemical identity of any such groups attached via this point of attachment is not important in view of the functioning of the invention, as further explained herein.

The compound comprising a moiety of formula (I) or (I') constitutes a conjugate through which a protein or peptide $R_1$ is linked (typically covalently) via a thiomaleamic acid linker moiety to a therapeutically active agent $R_2$. The inventors have found that this linker is stable under physiological conditions, but is susceptible to efficient cleavage at the pH conditions characterising the lysosome.

The thiomaleamic acid linker moiety

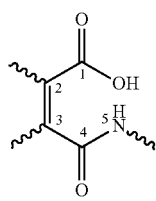

is believed to hydrolyse under acidic conditions in order to cleave the bond between the carbonyl group at the 4-position and the nitrogen atom at the 5-position. Thus, from the compounds of the present invention a fragment of the formula $H_2N-R_3-R_2$ may be produced by acid-catalysed hydrolysis. Surprisingly, the thiomaleamic acid linker moiety, bearing at least one electron donating thioether bond attached at the 2-position and/or the 3-position, has been found to undergo highly efficient hydrolysis typically in the pH range of 4 to 5, which corresponds precisely to the pH in the lysosome (for example, in human lysosomes in vivo).

It will be evident that the formulae (I) and (I') differ only in the location of the sulfur atom through which $R_1$ is linked to the thiomaleamic acid linker moiety. It is not important for the purposes of the present invention whether $R_1$ is attached via the 2-position as in formula (I), the 3-position as in formula (I'), or both the 2-position and the 3-position (as in the compound of formula (Ic)).

For the avoidance of doubt, the present invention includes within its scope compositions of matter that comprise (a) a compound comprising the moiety of formula (I) (including such compositions that contain substantially no compound comprising the moiety of formula (I')), or (b) a compound comprising the moiety of formula (I') (including such compositions that contain substantially no compound comprising the moiety of formula (I)), or (c) a mixture of a compound comprising the moiety of formula (I) and a compound comprising the moiety of formula (I'), or (d) any other mixture of compounds that fall within the definition of the formula (I) and/or (I').

In one embodiment, the protein or peptide is linked to the carbon-carbon double bond at the 2- and 3-positions of the moiety of formula (I) or (I') via a single sulfur atom (for purposes of clarity referred to herein as a "first sulfur atom"). Preferably in this embodiment, the compound comprising a moiety of formula (I) or (I') is a compound of formula (Ia) or (Ib):

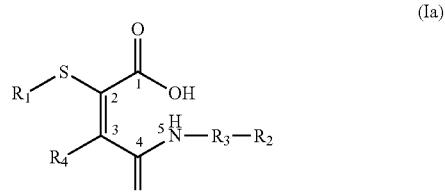

(Ia)

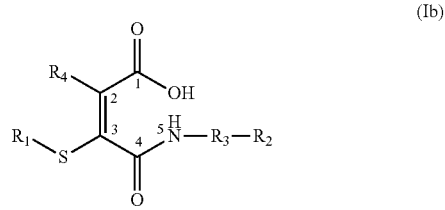

(Ib)

wherein:
$R_4$ is a hydrogen or halogen atom or a $C_{1-20}$ alkyl, $C_{2-20}$ alkenyl or $C_{2-20}$ alkynyl group, which group is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups are replaced by groups selected from —O—, —S—, —S—S—, —C(O)— and —N($C_{1-6}$ alkyl)- groups, wherein:
(i) said arylene, heteroarylene, carbocyclylene and heterocyclylene groups are unsubstituted or substituted by one or more substituents selected from halogen atoms and $C_{1-6}$ alkyl, $C_{1-6}$ alkoxy, $C_{1-6}$ alkylthiol, —N($C_{1-6}$ alkyl)($C_{1-6}$ alkyl), nitro and sulfonic acid groups; and (ii) 0, 1 or 2 carbon atoms in said carbocyclylene and heterocyclylene groups are replaced by —C(O)— groups;

$R_1$ being linked to the 2-position of the moiety of formula (Ia) via a first sulfur atom attached to the 2-position of the moiety of formula (Ia); and $R_1$ being linked to the 3-position of the moiety of formula (Ib) via a first sulfur atom attached to the 3-position of the moiety of formula (Ib).

In an alternative, and preferred, embodiment, the protein or peptide is linked to the carbon-carbon double bond at both the 2-position and the 3-position of the moiety of formula (I) or (I') (i.e., in a "bridging" arrangement), via two different sulfur atoms (for purposes of clarity referred to herein as a "first sulfur atom" and a "second sulfur atom"). Preferably in this embodiment, the compound comprising a moiety of formula (I) or (I') is a compound of formula (Ic):

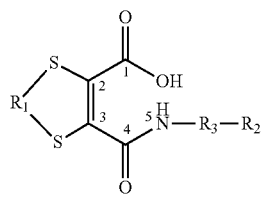

(Ic)

$R_1$ being linked to the 2-position of the moiety of formula (Ic) via a first sulfur atom attached to the 2-position of the moiety of formula (Ic) and $R_1$ being linked to the 3-position of the moiety of formula (Ic) via a second sulfur atom attached to the 3-position of the moiety of formula (Ic).

In the compound comprising a moiety of formula (I) or (I') (and necessarily also in the compounds of formulae (Ia), (Ib) and (Ic)), $R_1$ is said to be "linked" to the 2-position and/or the 3-position. "Linked" in this context should be construed broadly, and encompasses any means by which $R_1$ can directly or indirectly be attached, typically covalently, to the relevant position. For the avoidance of doubt, "attached" in this context therefore means directly bound, typically covalently bound. For example, a "first sulfur atom attached to the 2-position of the moiety of formula (I)" is as shown in the chemical structure, i.e. the sulfur atom is (covalently) directly bound to the carbon atom at the 2-position.

By contrast, "linked" means that $R_1$ may itself comprises a sulfur atom, which sulfur atom is attached to the relevant position (i.e., $R_1$ is directly attached through the said sulfur atom). Alternatively, $R_1$ may be attached to an intermediate "sub-linker" group, which sub-linker group comprises a sulfur atom, which sulfur atom is attached to the relevant position (i.e., $R_1$ is indirectly linked through the sub-linker group and then the said sulfur atom).

As workers in this field would be aware, "sub-linker" groups have commonly been used in ADCs to attach antibodies and antibody fragments to further linker groups, the latter linker groups being capable of cleaving in vivo to generate the desired therapeutic effect. For example, modification of lysine residues in antibodies with thiol-bearing linking groups (e.g., amide-alkyl-thiol reagents) has been used in order to render the said antibodies susceptible to functionalisation with conventional maleimide linkers.

The specific chemical identity of any such "sub-linker" group used in order to link $R_1$ via a sulfur atom to the 2- and/or the 3-position of the compounds of the present invention is not important and could be selected as a matter of routine by those skilled in the art using known techniques.

Preferably, however, in the compounds of the present invention $R_1$ is linked to the relevant position in the moiety of formula (I) or (I') by direct attachment of a sulfur atom in a cysteine residue of $R_1$ to that position. In other words, $R_1$ is preferably attached to the 2-position of the moiety of formula (I) (and (Ia)) via a first sulfur atom, which first sulfur atom is the sulfur atom of a first cysteine residue in $R_1$. Furthermore, $R_1$ is preferably attached to the 3-position of the moiety of formula (I') (and (Ib)) via a first sulfur atom, which first sulfur atom is the sulfur atom of a first cysteine residue in $R_1$. In compounds of formula (Ic), preferably $R_1$ is attached to the 2-position of the moiety of formula (Ic) via a first sulfur atom, which first sulfur atom is the sulfur atom of a first cysteine residue in $R_1$, and $R_1$ is also attached to the 3-position of the moiety of formula (Ic) via a second sulfur atom, which second sulfur atom is the sulfur atom of a second cysteine residue in $R_1$.

For the avoidance of doubt, a cysteine residue in a protein or peptide is a residue of formula

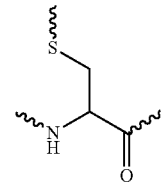

Attachment of $R_1$ via at least a first cysteine residue (e.g., a first cysteine residue and a second cysteine residue) can be seen to be particularly convenient, since it makes use of functional groups that are already present in the protein or peptide and therefore does not rely on preliminary functionalisation of $R_1$ prior to generation of the conjugate (e.g., by addition of a "sub-linker" such as those described above and/or the use of post-translational techniques to introduce non-native, sulfhydryl-containing amino acid residues).

Many proteins and peptides in their isolated forms contain disulfide bridges —S—S— which are formed by sulfur-sulfur bonding of the sulfur atoms of two different cysteine residues in the protein or peptide. Antibodies for example are well known to contain disulfide bridges that link together their discrete chains (known as interchain disulfides). The term "in isolated form" refers to the structure of the protein or peptide when it is not attached to the thiomaleamic acid linker (or otherwise functionalised).

In one preferred embodiment of the present invention, the compound is a compound of formula (Ic) in which the first sulfur atom is a first cysteine residue of $R_1$ and the second sulfur atom is a second cysteine residue of $R_1$ and the first sulfur atom and second sulfur atom are attached to one another via a disulfide bridge —S—S— when the protein or peptide is in isolated form. For example, when $R_1$ is an antibody or antibody fragment, preferably the said disulfide bridge is an interchain disulfide bridge. In this embodiment, the disulfide bridge that existed in the isolated protein or peptide can be seen to have been substituted by an analogue of such a bridge, i.e. the cyclic system comprising the carbons at the 2- and 3-positions of the moiety of formula (Ic) in conjunction with the sulfur atoms of the two cysteines linked via the underlying amino acid sequence of the protein or peptide $R_1$.

$R_1$ is typically a protein or peptide that is capable of specific binding to a target of interest, for example a target cell. Preferably $R_1$ is capable of specific binding to a cancer cell. Non-limiting examples of R1 include antibodies, antibody fragments, lectins, glycoproteins, growth factors, cytokines, interferons, interleukins, insulin and transferrin and any other protein or peptide that is capable of specific binding to a target cell of therapeutic interest.

Preferably, $R_1$ is an antibody or an antibody fragment. Preferably the antibody or antibody fragment is capable of specific binding to a target cell, for example a cancer cell.

The antibody may be polyclonal or monoclonal, but is preferably monoclonal. The antibody is preferably a chimeric, human or humanized antibody. The antibody fragment is preferably a Fab or an scFvs antibody fragment.

The present application is not a primer on antibodies. A worker skilled in the art of preparing bioconjugates, such as ADCs, would be familiar with working this antibodies and would readily be capable of selecting suitable antibodies or fragments thereof for designing specific compounds of the present invention. It will be appreciated that the specific identity of an antibody or antibody fragment may be determined by various criteria, a primary criterion being the intended therapeutic application and thus the target antigen. Typically where an ADC is intended to target a cell such as a cancer cell the antibody or antibody fragment will be selected so that its antigen is an antigen over-expressed by that cell with respect to expression on non-cancer cells, e.g. an antigen that is over-expressed on the surface of a particular type of cancer cell. This enables the ADC to be targeted specifically to the cells on which the therapeutic effect (e.g., a cytotoxic effect achieved via a cytotoxic therapeutically active agent) is desired.

In principle the thiomaleamic acid linker moiety is suitable for connecting any antibody/antibody fragment to any therapeutically active agent. Numerous ADCs have already been developed wherein an antibody/antibody fragment is conjugated to a therapeutically active agent via a known linker. Compounds of the present invention include compounds that comprise any of these previously known "pairs" of antibody/antibody fragment and therapeutically active agent, but modified to be conjugated via the thiomaleamic acid linker moiety.

Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing.

Non-limiting exemplary antibodies and antibody fragments for use in the present invention include antibodies and antibody fragments that are capable of specific binding to the following antigens (exemplary, but non-limiting, corresponding disease states being listed in parentheses): CA125 (ovarian), CA15-3 (carcinomas), CA19-9 (carcinomas), CA 242 (colorectal), L6 (carcinomas), CD2 (Hodgkin's Disease or non-Hodgkin's lymphoma), CD3, CD4, CD5, CD6, CD11, CD25, CD26, CD37, CD44, CD64, CD74, CD205, CD227, CD79, CD 105, CD138, CD20 (non-Hodgkin's lymphoma), CD52 (leukemia), CD33 (leukemia), CD22 (lymphoma), CD38 (multiple myeloma), CD40 (lymphoma), CD19 (non-Hodgkin's lymphoma), CD30 (CD30+ malignancies), CD70, CD56 (small-cell lung cancer, ovarian cancer, multiple myeloma, solid tumors), Lewis Y (carcinomas), Lewis X (carcinomas), human chorionic gonadotropin (carcinoma), alpha fetoprotein (carcinomas), placental alkaline phosphatase (carcinomas), prostate specific antigen (prostate), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1 (breast cancer), CEA (colorectal), gp100 (melanoma), MARTI (melanoma), IL-2 receptor (T-cell leukemia and lymphomas), mucin (carcinomas), P21 (carcinomas), MPG (melanoma), Neu oncogene product (carcinomas), BCMA, Glypican-3, Liv-1 or Lewis Y (epithelial tumors), HER2 (breast cancer), GPNMB (breast cancer), CanAg (solid tumors), DS-6 (breast cancer, ovarian cancer, solid tumors), HLA-Dr10 (non-Hodgkin's lymphoma), VEGF (lung and colorectal cancers), MY9, B4, EpCAM, EphA receptors, EphB receptors, EGFR, EGFRvIII, HER2, HER3, BCMA, PSMA, mesothelin, cripto, alpha(v)beta3, alpha(v)beta5, alpha(v)beta6 integrin, C242, EDB, TMEFF2, FAP, TAG-72, GD2, CAIX and 5T4.

Currently particularly preferred antibodies and antibody fragments include those capable of specific binding to the following antigens: MY9, B4, EpCAM, CD2, CD3, CD4, CD5, CD6, CD11, CD19, CD20, CD22, CD25, CD26, CD30, CD33, CD37, CD38, CD40, CD44, CD56, CD64, CD70, CD74, CD79, CD105, CD138, CD205, CD227, EphA receptors, EphB receptors, EGFR, EGFRvIII, HER2, HER3, BCMA, PSMA, Lewis Y, mesothelin, cripto, alpha (v)beta3, alpha(v)beta5, alpha(v)beta6 integrin, C242, CA125, GPNMB, ED-B, TMEFF2, FAP, TAG-72, GD2, CAIX and 5T4.

Examples of antibodies known for use in the treatment of cancer include RITUXAN® (rituximab; Genentech) which is a chimeric anti-CD20 monoclonal antibody for the treatment of patients with non-Hodgkin's lymphoma; OVAREX which is a murine antibody for the treatment of ovarian cancer; PANOREX (Glaxo Wellcome, NC) which is a murine $IgG_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; CAMPATH I/H (Leukosite, Mass.) which is a humanized $IgG_1$ antibody for the treatment of chronic lymphocytic leukemia (CLL); SMART MI95 (Protein Design Labs, Inc., CA) and SGN-33 (Seattle Genetics, Inc., WA) which is a humanized anti-CD 33 IgG antibody for the treatment of acute myeloid leukemia (AML); LYMPHOCIDE (Immunomedics, Inc., NJ) which is a humanized anti-CD22 IgG antibody for the treatment of non-Hodgkin's lymphoma; SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; AVASTIN (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; CEACIDE (Immunoniedics, NJ) which is a humanized anti-CEA antibody for the treatment of colorectal cancer; and Herceptin (TRASTUZUMAB), which is an anti-HER2/neu receptor monoclonal antibody for the treatment of breast cancer.

Preferably $R_2$ has greater therapeutic activity following hydrolysis of the moiety of formula (I) or (I') than when it forms part of the moiety of formula (I) or (I').

As is well known by those skilled in the art of synthesising ADCs, typically the therapeutically active agent "drug cargo" of the conjugate must be released from the ADC in order to exhibit its therapeutic activity. A skilled person would readily understand how to assess whether "greater therapeutic activity" is achieved when $R_2$ has been released by hydrolysis of the moiety of formula (I) or (I'). For example, the skilled person would be familiar with routine tests, such as in vitro tests, for example using standard cell lines that express a particular antigen of interest, that are used in the art to assess the potency of particular classes of therapeutically active agents. Such tests can be carried out on a comparative basis, i.e. by carrying out the test on both the compound comprising the moiety of formula (I) or (I') and on the hydrolysis product thereof (i.e., on $R_2$ or the hydrolysis fragment that retains the group $R_2$).

Typically, therefore $R_2$ is capable of exerting a therapeutic effect when the compound comprising a moiety of formula (I) or (I') has been internalised within a target cell and following hydrolysis of the moiety of formula (I) or (I') within said target cell (e.g., within the lysosome of said target cell).

Preferably $R_2$ is a cytotoxic agent. Preferred cytotoxic agents include anthracyclines, auristatins, maytansinoids, calicheamicins, taxanes, benzodiazepines and duocarmycins. As would be readily understood by those skilled in the art, the purpose of the cytotoxic agent is typically to exert a cytotoxic effect on the cancer cell following specific targeting thereof by $R_1$ and release of $R_2$ via cleavage of the thiomaleamic acid linker moiety in the lysosome.

Preferably $R_1$ is an antibody or antibody fragment that is capable of specific binding to a cancer cell and $R_2$ is a cytotoxic agent.

The compound comprising a moiety of formula (I) or (I') may comprise a further linker moiety $R_3$ that connects the nitrogen atom at the 5-position of the thiomaleamic acid moiety to the therapeutically active agent $R_2$. Alternatively $R_3$ may be a bond, i.e. the therapeutically active agent $R_2$ may be connected directly to the 5-position of the thiomaleamic acid moiety.

Typically the moiety of formula (I) or (I') is capable of hydrolyzing at a pH of from 4 to 5 to release a fragment of the formula $H_2N-R_3-R_2$. By "hydrolyzing at a pH of from 4 to 5" is meant hydrolyzing under aqueous conditions at at least one pH that lies in the range of 4 to 5 (e.g., at a temperature of 30-40° C. such as 37° C.). Typically the moiety of formula (I) or (I') is therefore capable of hydrolyzing in the lysosome of a subject, for example a human subject, in vivo, since the lysosomal environment is an aqueous environment having a pH in the region of 4 to 5.

It will be appreciated that while the therapeutically active agent is defined herein as the group $R_2$, it may in certain embodiments exert its therapeutic effect within the cell while still carrying for example a linker moiety $R_3$, a fragment of the linker moiety $R_3$ produced on hydrolysis of $R_3$ or the group $H_2N$— produced when $R_2$ is a bond and the thiomaleamic acid moiety undergoes hydrolysis. In other words, the therapeutic effect may be effected by a hydrolysis fragment of compound comprising the moiety of formula (I) or (I') that retains the group $R_2$. For the avoidance of doubt, the present invention explicitly includes compounds wherein the therapeutic effect is ultimately achieved not by a fully isolated therapeutically active agent $R_2$, but by a substance that comprises $R_2$ attached to a further moiety such as those described, provided of course that cleavage of the thiomaleamic acid linker moiety has occurred.

When $R_3$ is a linker moiety, the therapeutically active agent $R_2$ may be capable of achieving its therapeutic effect while still attached thereto (in which case $R_3$ does not itself need to hydrolyze to thereby release the therapeutically active agent). However, preferably when $R_3$ is a linker moiety, it is further capable of hydrolyzing to release the therapeutically active agent. By "release the therapeutically active agent" is meant that $R_3$ undergoes hydrolysis to release a fragment that consists of or comprises $R_2$, said fragment being capable of exhibiting the desired therapeutic effect.

Preferably if when $R_3$ is a linker moiety it is further capable of hydrolyzing to release the therapeutically active agent, said linker moiety is further capable of hydrolyzing at a pH of from 4 to 5. Again, by "hydrolyzing at a pH of from 4 to 5" is meant hydrolyzing under aqueous conditions at at least one pH that lies in the range of 4 to 5 (e.g., at a temperature of 30-40° C. such as 37° C.).

Preferably said linker moiety $R_3$ is not capable of hydrolyzing to release the therapeutically active agent at a pH of greater than 7, more preferably not greater than 6, most preferably not greater than 5.5.

For the avoidance of doubt, it is not important whether in the compound comprising a moiety of formula (I) or (I') in which $R_3$ is a linker moiety, said compound in practice initially hydrolyzes to release a fragment $H_2N-R_3-R_2$ which then undergoes further hydrolysis of the linker $R_3$ to release the therapeutically active agent, or whether in practice the first step in the disintegration of the compound is via hydrolysis of the linker $R_3$ to release the therapeutically active agent.

A preferred linker moiety $R_3$ is a linker moiety that is a $C_{1-20}$ alkylene group, a $C_{2-20}$ alkenylene group or a $C_{2-20}$ alkynylene group, which is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups are replaced by groups selected from —O—, —S—, —S—S—, —C(O)—, —NH—, —N($C_{1-6}$ alkyl)-, —O—C(O)—, —O—C(O)—NH—, —NH—C(O)— and —NH—C(O)—O— groups, wherein:

(i) said arylene, heteroarylene, carbocyclylene and heterocyclylene groups are unsubstituted or substituted by one or more substituents selected from halogen atoms and nitro, carboxyl, cyano, acyl, acylamino, carboxamide, sulfonamide, trifluoromethyl, phosphate, $C_{1-6}$ alkyl, $C_{6-10}$ aryl, 5- to 10-membered heteroaryl, $C_{3-7}$ carbocyclyl, 5- to 10-membered heterocyclyl, —$OR_x$, —$SR_x$, —$N(R_x)(R_y)$ and —$SO_2$—$R_x$ groups, wherein $R_x$ and $R_y$ are independently selected from hydrogen atoms and $C_{1-6}$ alkyl and $C_{6-10}$ aryl groups; and (ii) 0, 1 or 2 carbon atoms in said carbocyclylene and heterocyclylene groups are replaced by —C(O)— groups.

Preferably any arylene, heteroarylene, carbocyclylene and heterocyclylene groups are substituted by at most two substituents and more preferably they are unsubstituted. Preferred substituents include $C_{1-6}$ alkyl, —O($C_{1-6}$ alkyl), carboxamide and acyl.

When $R_3$ is a linker moiety it preferably contains a phenylene group attached to the nitrogen atom at the 5-position in the moiety of formula (I) or (I'), said phenylene group being unsubstituted or substituted by one or more substituents selected from halogen atoms and nitro, carboxyl, cyano, acyl, acylamino, carboxamide, sulfonamide, trifluoromethyl, phosphate, $C_{1-6}$ alkyl, $C_{6-10}$ aryl, 5- to 10-membered heteroaryl, $C_{3-7}$ carbocyclyl, 5- to 10-membered heterocyclyl, —$OR_x$, —$SR_x$, —$N(R_x)(R_y)$ and —$SO_2$—$R_x$ groups, wherein $R_x$ and $R_y$ are independently selected from hydrogen atoms and $C_{1-6}$ alkyl and $C_{6-10}$ aryl groups.

The presence of phenylene group increases the hydrolysis reactivity at a pH of from 4 to 5 of the compound comprising a moiety of formula (I) or (I') by rendering the fragment —N(H)—$R_3$—$R_2$ a better leaving group. Preferred substituents for the phenylene group include $C_{1-6}$ alkyl, —O($C_{1-6}$ alkyl), carboxamide and acyl. Preferably the phenylene group is substituted by at most two substituents and more preferably the phenylene group is unsubstituted.

When $R_3$ is a linker moiety it preferably is a linker moiety that, together with the group $R_2$, comprises a carbamate moiety of formula —O—C(O)—N(H)— or —N(H)—C(O)—O—. As is well known in organic synthetic chemistry, a carbamate moiety is susceptible to hydrolysis to release a hydroxyl-functionalised fragment, an amine-functionalised fragment, and carbon dioxide.

Preferably when $R_3$ is a linker moiety it has the formula -[A]-[B]-[C]-, wherein:
[A] is a phenylene group that is unsubstituted or substituted by one or more substituents selected from halogen atoms and nitro, carboxyl, cyano, acyl, acylamino, carboxamide, sulfonamide, trifluoromethyl, phosphate, $C_{1-6}$ alkyl, $C_{6-10}$ aryl, 5- to 10-membered heteroaryl, $C_{3-7}$ carbocyclyl, 5- to 10-membered heterocyclyl, —$OR_x$, —$SR_x$, —$N(R_x)(R_y)$ and —$SO_2$—$R_x$ groups, wherein $R_x$ and $R_y$ are independently selected from hydrogen atoms and $C_{1-6}$ alkyl and $C_{6-10}$ aryl groups;
[B] is a bond or a $C_{1-6}$ alkyl group; and
[C] is a group of formula —O—C(O)—NH—, —O—C(O)—, —N(H)—C(O)—O— or —N(H)—C(O)—, such that the fragment [C]—[$R_2$]— is attached to the fragment -[A]-[B]- via a carbamate moiety of formula —O—C(O)—N(H)— or —N(H)—C(O)—O—.

Preferred substituents for the phenylene group [A] include $C_{1-6}$ alkyl, —O($C_{1-6}$ alkyl), carboxamide and acyl. Preferably [A] is a phenylene group having at most two substituents, and most preferably said phenylene group is unsubstituted.

An exemplary linker moiety $R_3$ has the formula

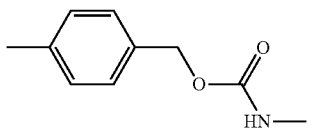

Typically when $R_3$ is a bond, the moiety of formula (I) or (I') is capable of hydrolyzing at a pH of from 4 to 5 to release a fragment of the formula $H_2N$—$R_2$. Again, by "hydrolyzing at a pH of from 4 to 5" is meant hydrolyzing under aqueous conditions at at least one pH that lies in the range of 4 to 5 (e.g., at a temperature of 30-40° C. such as 37° C.).

Preferably the compound comprising a moiety of formula (I) or (I') is not capable of hydrolyzing to release the therapeutically active agent or a fragment of formula $H_2N$—$R_3$—$R_2$ or $H_2N$—$R_2$ at a pH of 7 or higher, more preferably not 6 or higher, most preferably not higher than 5.5.

In one currently preferred aspect, $R_1$ is an antibody or antibody fragment that is capable of specific binding to a cancer cell, such as those herein defined, $R_2$ is a cytotoxic agent, such as those herein defined, and $R_3$ is a linker moiety such as those herein defined and that: (i) contains a phenylene group attached to the nitrogen atom at the 5-position in the moiety of formula (I) or (I'), said phenylene group being unsubstituted or substituted by one or more substituents selected from halogen atoms and nitro, carboxyl, cyano, acyl, acylamino, carboxamide, sulfonamide, trifluoromethyl, phosphate, $C_{1-6}$ alkyl, $C_{6-10}$ aryl, 5- to 10-membered heteroaryl, $C_{3-7}$ carbocyclyl, 5- to 10-membered heterocyclyl, —$OR_x$, —$SR_x$, —$N(R_x)(R_y)$ and —$SO_2$—$R_x$ groups, wherein $R_x$ and $R_y$ are independently selected from hydrogen atoms and $C_{1-6}$ alkyl and $C_{6-10}$ aryl groups; and/or (preferably and) (ii) (ii) together with the group $R_2$, comprises a carbamate moiety of formula —O—C(O)—N(H)— or —N(H)—C(O)—O—.

Particularly preferably $R_1$ is an antibody or antibody fragment that is capable of specific binding to a cancer cell, such as those herein defined, $R_2$ is a cytotoxic agent, such as those herein defined, and $R_3$ is a linker moiety of the formula -[A]-[B]-[C]-, as herein defined.

In the compound of formula (Ia) or (Ib) $R_4$ is preferably a hydrogen or halogen atom or an unsubstituted $C_{1-6}$ alkyl, $C_{2-6}$ alkenyl or $C_{2-6}$ alkynyl group, in which (a) 0 or 1 carbon atom is replaced by a group selected from phenylene, 5- to 6-membered heteroarylene, $C_{5-6}$ carbocyclylene and 5- to 6-membered heterocyclylene groups, wherein said phenylene, heteroarylene, carbocyclylene and heterocyclylene groups are unsubstituted or substituted by one or two substituents selected from halogen atoms and $C_{1-4}$ alkyl and $C_{1-4}$ alkoxy groups, and (b) 0, 1 or 2 —$CH_2$— groups are replaced by groups selected from —O—, —S— and —C(O)— groups.

More preferably, $R_4$ represents a hydrogen atom or an unsubstituted $C_{1-6}$ alkyl group, in which (a) 0 or 1 carbon atom is replaced by a group selected from unsubstituted phenylene, 5- to 6-membered heteroarylene, $C_{5-6}$ carbocyclylene and 5- to 6-membered heterocyclylene groups.

Most preferably $R_4$ is a hydrogen atom or an unsubstituted $C_{1-6}$ alkyl group.

The compounds comprising a moiety of formula (I) or (I') can be produced using routine techniques known in the art for attaching cross-linker reagents to functional moieties, such as those described in "Bioconjugate Techniques" (Greg T. Hermanson, Academic Press Inc., 1996), the content of which is herein incorporated by reference in its entirety. Further examples of suitable conditions for carrying out such reactions can be found in the Examples section of the present specification.

As would be understood by those of skill in the art, where a reagent carries more than one reactive group, it may be desirable to effect chemical protection of reactive groups that are not intended to take part in the reaction. For example, it may be necessary to protect groups such as hydroxyl, amino and carboxy groups, where these are desired in the final product, to avoid their unwanted participation in the reactions (see, for example, Greene, T. W., "Protecting Groups in Organic Synthesis", John Wiley and Sons, 1999). Conventional protecting groups may be used in conjunction with standard practice.

One preferred method for producing compounds comprising a moiety of formula (I) or (I') involves hydrolyzing a corresponding thiomaleimide-linked conjugate of formula (II)

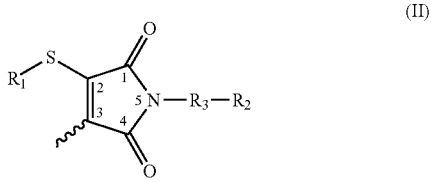

(II)

wherein $R_1$, $R_3$ and $R_2$ are as herein defined. It will be appreciated that hydrolysis of the thiomaleimide-linked conjugate of formula (II) can generate a compound comprising a moiety of formula (I) and/or a compound comprising a moiety of formula (I'), depending on the degree of regioselectivity of the hydrolysis. If desired, regioselectivity can be achieved using known techniques such as the use of additional substituents (e.g., at the 3-position in the formula (II)) to direct the site at which hydrolysis is initiated (for example by nucleophilic attack at either the 1-position or the 4-position in the formula (II)). For example, electron-donating, electron-withdrawing, or sterically-hindering substituents may be sited at the 3-position of the formula (II). If required, a mixture of a compound comprising a moiety of formula (I) and a compound comprising a moiety of formula (I') as formed by hydrolysis of the conjugate of the formula (II) can be purified using conventional methods; alternatively such a mixture can typically be used as is.

Compounds of the formulae (Ia) and (Ib) can thus be readily made by hydrolysis of corresponding compounds of formulae (IIa) below.

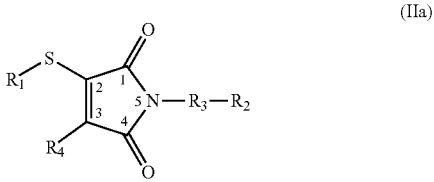

(IIa)

Further, compounds of the formulae (Ic) can be readily made by hydrolysis of corresponding compounds of formulae (IIc) below.

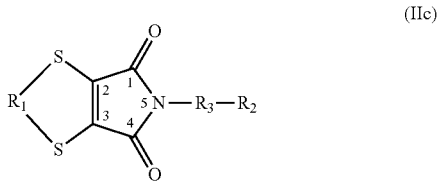

(IIc)

Methods for making compounds having the general structures (II), (IIa) and (IIc) are described in detail in WO 2011/018611, the content of which is herein incorporated by reference in its entirety.

Hydrolysis of such compounds to produce compounds of the present invention can be effected using known techniques for hydrolysis of maleimide compounds into maleaimic acid compounds (see for example Machida et al., Chem. Pharm. Bull. 1977 24 2739 and Ryan et al. Chem. Commun 2011 47 5452). One suitable method is to subject the compound of formula (II), (IIa) or (IIc) to mildly basic aqueous conditions (e.g., a pH of 7.1 or higher, for example 7.2 to 10), at a temperature of from 0 to 50° C. (e.g., from 20 to 40° C.). Any base or basic buffer solution could be used. LiOH is one suitable example. A PBS buffer solution at a pH of 7.4 is also effective.

The pharmaceutical composition of the present invention is suitable for veterinary or human administration.

The present pharmaceutical compositions can be in any form that allows for the composition to be administered to a patient. The composition may for example be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Compositions can take the form of one or more dosage units, where for example, a tablet can be a single dosage unit, and a container of a compound of the present invention in liquid form can hold a plurality of dosage units.

Materials used in preparing the pharmaceutical compositions are preferably non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound of the present invention, the manner of administration, and the composition employed.

The pharmaceutically acceptable diluent or carrier can be solid or particulate, so that the compositions are, for example, in tablet or powder form. The carrier(s) can be liquid. In addition, the carrier(s) can be particulate.

The pharmaceutical composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

Liquid pharmaceutical compositions, whether they are solutions, suspensions or other like form, can also include one or more of the following; sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the compound comprising a moiety of formula (I) or (I') that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound comprising a moiety of formula (I) or (I') such that a suitable dosage will be obtained. Typically, this amount is at least about 0.01% of compound comprising a moiety of formula (I) or (I') by weight of the composition. In an exemplary embodiment, pharmaceutical compositions are prepared so that a parenteral dosage unit contains from about 0.01% to about 2% by weight of the compound comprising a moiety of formula (I) or (I').

For intravenous administration, the composition can comprise from about 0.01 to about 100 mg of a compound comprising a moiety of formula (I) or (I') per kg of the patient's body weight. In one aspect, the composition can include from about 1 to about 100 mg of a compound comprising a moiety of formula (I) or (I') per kg of the patient's body weight. In another aspect, the amount administered will be in the range from about 0.1 to about 25 mg/kg of body weight of the compound comprising a moiety of formula (I) or (I').

Generally, the dosage of compound comprising a moiety of formula (I) or (I') administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

The compound comprising a moiety of formula (I) or (I') can be administered by any convenient route, for example by infusion or bolus injection. Administration can be systemic or local. Various delivery systems are known, e.g., encapsulation in liposomes, microparticles, microcapsules, capsules, etc., and can be used to administer a compound comprising a moiety of formula (I) or (I'). In certain embodiments, more than one compound comprising a moiety of formula (I) or (I') is administered to a patient.

In specific embodiments, it can be desirable to administer one or more compound comprising a moiety of formula (I) or (I') locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue, in another embodiment, administration can be by direct injection at the site (or former site) of a manifestation of an autoimmune disease.

The compound comprising a moiety of formula (I) or (I') can be delivered in a controlled release system, such as but not limited to, a pump or various polymeric materials can be used. Also, a controlled-release system can be placed in proximity of the target of the compound comprising a moiety of formula (I) or (I'), e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier or diluent" refers to a diluent, adjuvant or excipient, with which a compound comprising a moiety of formula (I) or (I') is administered. Such pharmaceutical carriers can be liquids, such as water and oils, including those of petroleum, animal, vegetable or synthetic origin. The carriers can be saline, and the like. In addition, auxiliary, stabilizing and other agents can be used. Preferably, when administered to a patient, the compound comprising a moiety of formula (I) or (I') and pharmaceutically acceptable carriers are sterile. Water is an exemplary carrier when the compound comprising a moiety of formula (I) or (I') is administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use. Other examples of suitable pharmaceutical carriers are described in "Remington's Pharmaceutical Sciences" by E. W. Martin.

The compound comprising a moiety of formula (I) or (I') may be formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a compound comprising a moiety of formula (I) or (I') is to be administered by infusion, it can be dispensed, for example, with an infusion bottle containing sterile pharmaceutical grade water or saline. Where the compound comprising a moiety of formula (I) or (I') is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer.

The compounds comprising a moiety of formula (I) or (I') are particularly useful for treating cancer. Specifically, the compound comprising a moiety of formula (I) or (I') is useful for inhibiting the multiplication of a tumor cell or cancer cell, causing apoptosis in a tumor or cancer cell, or for treating cancer in a patient. The compounds comprising a moiety of formula (I) or (I') can be used accordingly in a variety of settings for the treatment of animal cancers.

The compound comprising a moiety of formula (I) or (I') can be used to deliver a therapeutically active agent to a tumor cell or cancer cell. The compounds of the present invention can thus be used in a method of ameliorating or reducing the incidence of cancer (such as those defined herein) in a subject, which method comprises the administration to the said subject of an effective amount of a compound comprising a moiety of formula (I) or (I') and wherein $R_1$ is an antibody or antibody fragment that is capable of specific binding to an antigen present on a cancerous cell and $R_2$ is a cytotoxic agent.

Examples of types of cancers that can be treated with a compound comprising a moiety of formula (I) or (I') include, but are not limited to:

Solid tumors, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma and retinoblastoma, blood-borne cancers, including but not limited to acute lymphoblastic leukemia "ALL", acute lymphoblastic B-cell leukemia, acute lymphoblastic T-cell leukemia, acute myeloblastic leukemia "AML", acute promyelocyte leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukaemia and multiple myelomal acute and chronic leukemias such as lymphoblastic, myelogenous, lymphocytic and myelocytic leukemias; and lymphomas such as Hodgkin's disease, non-Hodgkin's Lymphoma, Multiple myeloma, Waldenstrom's macroglobulinemia, Heavy chain disease and Polycythemia vera.

Further examples of cancers susceptible to treatment according to the present invention are those herein disclosed in parentheses in conjunction with specific antibodies or antibody fragments as herein disclosed.

The present invention further provides a compound comprising a moiety of formula (I) or (I') for use in a method of treatment of the human or animal body by therapy. Typically the method of treatment is a method of treatment of cancer, wherein $R_1$ is an antibody or antibody fragment that is capable of specific binding to an antigen present on a cancerous cell and $R_2$ is a cytotoxic agent. Types of cancer are again those outlined elsewhere herein.

The following Examples, which do not limit the scope of the invention, further illustrate the principles of the present invention.

EXAMPLES

Reference Example 1: Synthesis of Maleimide and Thiomaleamic Acid Reagents 2,3-dibromo-maleic anhydride (1)

Under an inert atmosphere, a mixture of maleic anhydride (1.50 g, 15.3 mmol), $AlCl_3$ (0.30 g, 0.21 mmol) and $Br_2$ (1.57 mL, 30.6 mmol) was heated at 160° C. in a sealed ampule for 20 h. Upon cooling to room temperature the reaction mixture was carefully opened to air, EtOAc was added the solid filtered off and repeatedly washed with further EtOAc. The filtrate was finally concentrated in vacuo to give the title compound (I) as a yellow solid (3.25 g, 12.8 mmol, 83%).

m.p. 107-110° C.; $v_{max}$ (cm$^{-1}$) 1769, 1706, 1590; $\delta_C$ (CDCl$_3$, 125 MHz) 164.4 (s), 125.9 (s); HRMS (CI) calculated for $C_4O_3Br_2$ [M]$^+$ 253.82087, observed: 253.82082.

N-phenyl-dibromomaleimide (2)

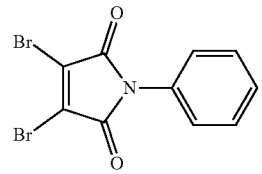 [SMILES: O=C1C(Br)=C(Br)C(=O)N1c1ccccc1]

2,3-dibromo-maleic anhydride 1 (0.50 g, 1.97 mmol) was dissolved in AcOH (25 mL) and aniline (0.180 mL, 1.97 mmol) was added. The mixture was stirred at room temperature for 3 h and then at 130° C. for 90 min. Then the mixture was concentrated to dryness and traces of AcOH were removed by repetitive addition and concentration of toluene. The crude residue was purified by flash chromatography to give the title compound as a pale yellow solid (0.37 g, 1.12 mmol, 57%).

$R_f$ 0.35 (10% EtOAc/petroleum ether); m.p. 136-138° C.; $v_{max}$ (cm$^{-1}$) 3058, 1727, 1715, 1646, 1610, 1598, 1501, 1382, 1265, 1113; $\delta_H$ (CDCl$_3$, 500 MHz) 7.48-747 (2H, m, ArH), 7.44-7.40 (1H, m, ArH), 7.33 (2H, d, J=7.2 Hz, ArH); $\delta_C$ (CDCl$_3$, 150 MHz) 163.0, 132.8, 130.8, 129.5, 128.8, 126.2; HRMS (EI) calculated for $C_{10}H_5O_2NBr_2$ 328.86816, observed 328.86854.

N-phenyl-diethylthiolmaleimide (3)

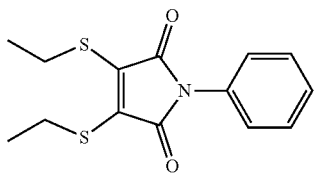 [SMILES: CCSC1=C(SCC)C(=O)N(c2ccccc2)C1=O]

To a solution of N-phenyl-dibromomaleimide 2 (237 mg, 0.72 mmol) in DCM (30 mL) were added ethanethiol (0.11 mL, 1.50 mmol) and NEt$_3$ (0.21 mL, 1.50 mmol) and the mixture was stirred for 15 min at room temperature and then concentrated to dryness. The crude residue was purified by flash chromatography to give the desired product (195 mg g, 0.66 mmol, 93%).

$R_f$ 0.36 (10% EtOAc/petroleum ether); $v_{max}$ (cm$^{-1}$) 2965, 2926, 2851, 1706, 1598, 1501, 1371; $\delta_H$ (CDCl$_3$, 600 MHz) 7.48-7.44 (2H, m, ArH), 7.37-7.33 (3H, m, ArH), 3.37 (4H, q, J=7.4 Hz, CH$_3$CH$_2$S), 1.38 (6H, t, J=7.4 Hz, CH$_3$CH$_2$S); $\delta_C$ (CDCl$_3$, 150 MHz) 165.5, 135.7, 131.6, 129.2, 128.0, 126.2, 26.5, 15.8; HRMS (EI) calculated for C$_{14}$H$_{15}$O$_2$NS$_2$ 293.05387, observed 293.05403.

N-methoxycarbonyl-dibromomaleimide (4)

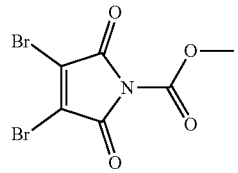

To a solution of dibromomaleimide (1.00 g, 3.9 mmol) and N-methylmorpholine (0.433 mL, 3.9 mmol) in THF (35 mL) was added methylchloroformate (0.304 mL, 3.9 mmol) and the mixture was stirred for 20 min at room temperature. Then CH$_2$Cl$_2$ (40 mL) was added, the organic phase was washed with H$_2$O, dried over MgSO$_4$ and the solvent removed in vacuo to yield the desired product as a pink powder (1.18 g, 3.8 mmol, 97%).

m.p. 115-118° C.; $v_{max}$ (cm$^{-1}$) 3236, 2962, 1809, 1769, 1730, 1602; $\delta_H$ (CDCl$_3$, 500 MHz) 4.00 (3H, s, CH$_3$); $\delta_C$ (CDCl$_3$, 125 MHz) 159.3, 147.0, 131.5, 54.9; MS (CI) m/z (%) 314 (M$^+$H, 100), 206 (13), 111 (12); Mass calculated for C$_6$H$_3$O$_4$N$^{79}$Br$_2$: 310.8423, observed: 310.8427.

N-hydroxymethylphenyl-dibromomaleimide (5)

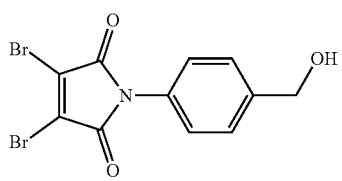 [SMILES: O=C1C(Br)=C(Br)C(=O)N1c1ccc(CO)cc1]

To a solution of N-methoxycarbonyl-dibromomaleimide 4 (300 mg, 0.965 mmol) in DCM (42 mL) was added 4-aminobenzylalcohol (119 mg, 0.965 mmol). After 2 h of stirring at room temperature the mixture was concentrated to dryness and the crude residue was purified by flash chromatography to give the desired compound as a yellow solid (345 mg, 0.955 mmol, 99%).

$R_f$ 0.53 (70% EtOAc/petroleum ether); m.p. 217-220° C.; $v_{max}$ (cm$^{-1}$) 3364, 1732, 1714, 1610, 1519, 1403, 809; $\delta_H$ (CDCl$_3$, 600 MHz) 7.49 (2H, d, J=8.4 Hz, ArH), 7.33 (2H, d, J=8.4 Hz, ArH), 4.75 (2H, s, CH$_2$OH); $\delta_C$ (CDCl$_3$, 150 MHz) 163.0, 141.6, 130.2, 130.0, 127.8, 126.3, 64.7; Mass calculated for C$_{11}$H$_7$O$_3$NBr$_2$: 358.87871, observed: 358.87983.

N-hydroxymethylphenyl-diethylthiolmaleimide (6)

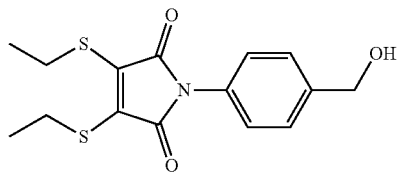 [SMILES: CCSC1=C(SCC)C(=O)N(c2ccc(CO)cc2)C1=O]

To a solution of N-hydroxymethylphenyl-dibromomaleimide 5 (315 mg, 0.872 mmol) in DCM (40 mL) were added ethanethiol (0.18 mL, 2.33 mmol) and NEt$_3$ (0.33 mL, 2.33 mmol) and the mixture was stirred for 1 h at room temperature and then concentrated to dryness. The crude residue was purified by flash chromatography to afford the desired compound as a yellow solid (242 mg, 0.748 mmol, 86%).

$R_f$ 0.55 (70% EtOAc/petroleum ether); m.p. 50-52° C.; $v_{max}$ (cm$^{-1}$) 3381, 2967, 2928, 2869, 1702, 1514, 1373, 1190; $\delta_H$ (CDCl$_3$, 600 MHz) 7.45 (2H, d, J=8.4 Hz, ArH), 7.33 (2H, d, J=8.4 Hz, ArH), 4.72 (2H, s, CH$_2$OH), 3.37 (4H, q, J=7.4 Hz, CH$_3$CH$_2$S), 1.37 (6H, t, J=7.4 Hz, CH$_3$CH$_2$S); $\delta_C$ (CDCl$_3$, 150 MHz) 165.5, 140.7, 135.7, 130.9, 127.6, 126.3, 64.9, 26.5, 15.8; Mass calculated for C$_{15}$H$_{17}$O$_3$NS$_2$: 323.06443, observed: 323.06342.

p-(diethylthiolmaleimide)-benzyl phenylcarbamate (7)

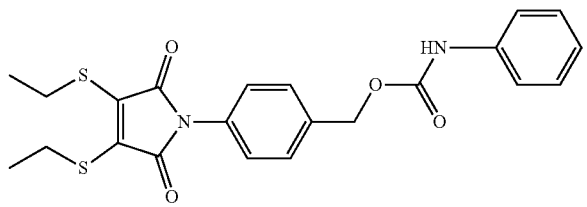 [SMILES: CCSC1=C(SCC)C(=O)N(c2ccc(COC(=O)Nc3ccccc3)cc2)C1=O]

To a solution of N-hydroxymethylphenyl-diethylthiolmaleimide 6 (100 mg, 0.309 mmol) in DCM (14 mL) were added phenylisocyanate (0.035 mL, 0.322 mmol) and NEt$_3$ (0.091 mL, 0.653 mmol) and the mixture was stirred for 2 days at room temperature and then concentrated to dryness. The crude residue was purified by flash chromatography to afford the desired compound as a yellow solid (84 mg, 0.190 mmol, 62%).

$R_f$ 0.69 (50% EtOAc/petroleum ether); m.p. 97-99° C.; $v_{max}$ (cm$^{-1}$) 3374, 2964, 2928, 1733, 1705, 1598, 1532, 1444, 1378, 1208; $\delta_H$ (CDCl$_3$, 600 MHz) 7.49 (2H, d, J=8.3

Hz, ArHCH$_2$O), 7.39-7.35 (4H, m, ArHCH$_2$O and ArHNH), 7.32-7.30 (2H, m, ArHNH), 7.07 (1H, t, J=7.4 Hz, ArHNH), 6.66 (1H, br s, NH), 5.22 (2H, s, CH$_2$OCONH), 3.37 (4H, q, J=7.4 Hz, CH$_3$CH$_2$S), 1.37 (6H, t, J=7.4 Hz, CH$_3$CH$_2$S); δ$_C$ (CDCl$_3$, 150 MHz) 165.4, 153.2, 137.7, 135.8, 131.6, 129.2, 129.1, 126.3, 126.2, 123.7, 118.8, 66.4, 26.5, 15.8; Mass calculated for C$_{22}$H$_{22}$N$_2$O$_4$NaS$_2$: 465.0919, observed: 465.0923.

2,3-diethylthiol-maleic anhydride (8)

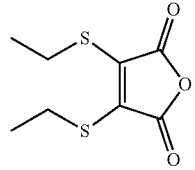

N-Phenyl-diethylthiolmaleimide 3 (19.0 mg, 0.065 mmol) was dissolved in a mixture of CD$_3$OD/D$_2$O 1/1 (2 mL) and LiOH (146 mg, 3.48 mmol) was added. The solution was stirred at room temperature for 24 h to generate the desired maleamic acid, lithium salt.

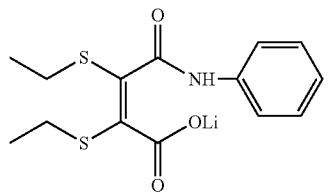

δ$_H$ (CD$_3$OD, 600 MHz) 7.46 (2H, d, J=7.8 Hz, ArH), 7.38 (2H, t. J=7.8 Hz, ArH), 7.18 (1H, t, J=7.8 Hz, ArH), 2.90 (2H, q, J=7.5 Hz, CH$_3$CH$_2$S), 2.80 (2H, q, J=7.5 Hz, CH$_3$CH$_2$S), 1.31 (3H, t, J=7.5 Hz, CH$_3$CH$_2$S), 1.29 (3H, t, J=7.5 Hz, CH$_3$CH$_2$S; δ$_C$ (CD$_3$OD, 150 MHz) 171.7, 166.0, 156.9, 139.6, 130.4, 130.3, 126.3, 122.8, 122.7, 119.9, 28.9, 28.0, 15.7, 15.3.

The solution was then acidified with 2N HCl to pH 4 and extracted with EtOAc. The resulting organic layer was washed with brine, dried over MgSO$_4$, filtered and concentrated to obtain 8 (14.0 mg, 0.065 mmol 100%).

ν$_{max}$ (cm$^{-1}$) 2969, 2930, 1761, 1518, 1379, 1244; δ$_H$ (CDCl$_3$, 600 MHz) 3.37 (4H, q, J=7.4 Hz, CH$_3$CH$_2$S), 1.36 (6H, t, J=7.4 Hz, CH$_3$CH$_2$S); δ$_C$ (CDCl$_3$, 150 MHz) 160.4, 136.9, 26.5, 15.8; HRMS (EI) calculated for C$_8$H$_{10}$O$_3$S$_2$ 218.00659, observed 218.00712.

2,3-diethylthiol-maleic anhydride (8)

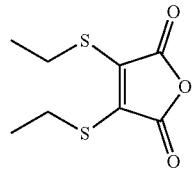

N-Hydroxymethylphenyl-diethylthiolmaleimide 6 (17.5 mg, 0.054 mmol) was dissolved in a mixture of CD$_3$OD/ D$_2$O 1/1 (1.6 mL) and LiOH (102 mg, 2.44 mmol) was added. The solution was stirred at room temperature for 30 min to generate the desired maleamic acid, lithium salt.

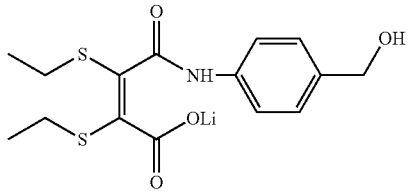

δ$_H$ (CD$_3$OD, 600 MHz) 7.44 (2H, d, J=8.7 Hz, ArH), 7.36 (2H, d, J=8.7 Hz, ArH), 4.59 (2H, s, CH$_2$OH), 2.90 (2H, q, J=7.2 Hz, CH$_3$CH$_2$S), 2.80 (2H, q, J=7.2 Hz, CH$_3$CH$_2$S), 1.31 (3H, t, J=7.2 Hz, CH$_3$CH$_2$S), 1.29 (3H, t, J=7.2 Hz, CH$_3$CH$_2$S).

The solution was then acidified with 2N HCl to pH 4 and extracted with EtOAc. The resulting organic layer was washed with brine, dried over MgSO$_4$, filtered and concentrated to obtain 8 (11.6 mg, 0.053 mmol 98%).

2,3-diethylthiol-maleic anhydride (8)

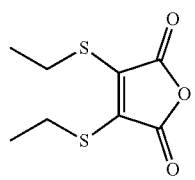

p-(diethylthiolmaleimide)-benzyl phenylcarbamate 7 (19.5 mg, 0.044 mmol) was dissolved in a mixture of CD$_3$OD/D$_2$O 1/1 (1.6 mL) and LiOH (102 mg, 2.44 mmol) was added. The solution was stirred at room temperature for 2 h to generate the desired maleamic acid, lithium salt.

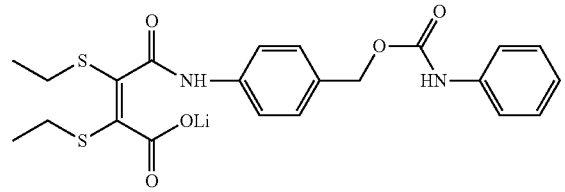

δ$_H$ (CD$_3$OD, 600 MHz) 7.52 (2H, d, J=8.3 Hz, ArHCH$_2$O), 7.41 (2H, d, J=8.3 Hz, ArHCH$_2$O), 7.38-7.36 (2H, m, ArHNH), 7.31 (2H, t, J=7.2 Hz, ArHNH), 7.07 (1H, t, J=7.2 Hz, ArHNH), 5.14 (2H, s, CH$_2$OCONH), 2.91 (2H, q, J=7.5 Hz, CH$_3$CH$_2$S), 2.79 (2H, q, J=7.5 Hz, CH$_3$CH$_2$S), 1.30 (3H, t, J=7.5 Hz, CH$_3$CH$_2$S), 1.28 (3H, t, J=7.5 Hz, CH$_3$CH$_2$S).

The solution was then acidified with 2N HCl to pH 4 and the mixture was stirred overnight. Then it was extracted with EtOAc and the resulting organic layer was washed with brine, dried over MgSO$_4$, filtered and concentrated to obtain 8 (9.6 mg, 0.044 mmol 100%).

p-(diethylthiolmaleimide)-benzyl 4-nitrophenyl carbonate (9)

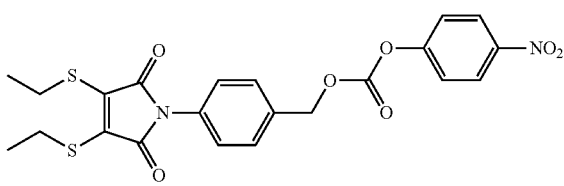 [SMILES: CCSC1=C(SCC)C(=O)N(c2ccc(COC(=O)Oc3ccc([N+](=O)[O-])cc3)cc2)C1=O]

To a solution of N-hydroxymethylphenyl-diethylthiolmaleimide 6 (40 mg, 0.124 mmol) in dry THF (3 mL) were added 4-nitrophenylchloroformate (30 mg, 0.148 mmol) and pyridine (0.012 mL, 0.148 mmol) and the mixture was stirred for 24 h at room temperature. Then EtOAc (10 mL) and 10% aqueous citric acid (10 mL) were added and the organic layer was washed with $H_2O$ and brine, dried over $MgSO_4$, filtered and concentrated. The crude residue was purified by flash chromatography to afford the title compound (52 mg, 0.106 mmol, 86%).

$R_f$ 0.68 (50% EtOAc/petroleum ether); $v_{max}$ (cm$^{-1}$) 3386, 2929, 1707, 1593, 1516, 1499, 1339, 1289, 1111; $\delta_H$ (CDCl$_3$, 600 MHz) 8.26 (2H, d, J=8.4 Hz, ArHNO$_2$), 7.52 (2H, d, J=8.4 Hz, ArHNO$_2$), 7.39 (2H, d, J=8.5 Hz, ArHCH$_2$O), 7.36 (2H, d, J=8.5 Hz, ArHCH$_2$O), 5.30 (2H, s, CH$_2$OCO$_2$), 3.36 (4H, q, J=7.4 Hz, CH$_3$CH$_2$S), 1.37 (6H, t, J=7.4 Hz, CH$_3$CH$_2$S); $\delta_C$ (CDCl$_3$, 150 MHz) 165.4, 155.6, 152.5, 145.5, 135.8, 133.8, 132.3, 129.5, 126.5, 125.2, 122.0, 70.3, 26.5, 15.8; Mass calculated for $C_{22}H_{20}O_7N_2S_2$: 488.07064, observed: 488.06954.

N-hydroxymethylphenyl-diphenylthiolmaleimide (10)

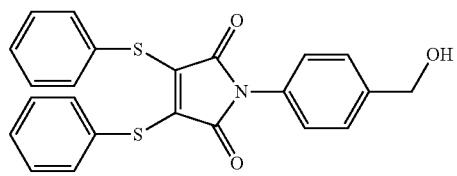 [SMILES: O=C1C(Sc2ccccc2)=C(Sc2ccccc2)C(=O)N1c1ccc(CO)cc1]

To a solution of N-hydroxymethylphenyl-dibromomaleimide 5 (139 mg, 0.385 mmol) in DCM (18 mL) was added NEt$_3$ (0.145 mL, 1.04 mmol) and phenylthiol (0.08 mL, 0.809 mmol) and the mixture was stirred for 30 min at room temperature and then concentrated to dryness. The crude residue was purified by flash chromatography to afford a yellow solid (159 mg, 0.378 mmol, 98%).

$R_f$ 0.63 (70% EtOAc/petroleum ether); m.p. 111-113° C.; $v_{max}$ (cm$^{-1}$) 3388, 3057, 2928, 2874, 1705, 1515, 1381, 735; $\delta_H$ (CDCl$_3$, 600 MHz) 7.46 (2H, d, J=8.4 Hz, ArHCH$_2$OH), 7.32 (2H, d, J=8.4 Hz, ArHCH$_2$OH), 7.31-7.26 (5H, m, ArHS), 4.70 (2H, s, CH$_2$OH); $\delta_C$ (CDCl$_3$, 150 MHz) 165.8, 140.7, 135.8, 132.2, 130.8, 129.2, 128.8, 128.7, 127.6, 126.1, 64.9; Mass calculated for $C_{23}H_{17}O_3NS_2$: 419.06498, observed: 419.06531.

p-(diphenylthiolmaleimide)-benzyl phenylcarbamate (11)

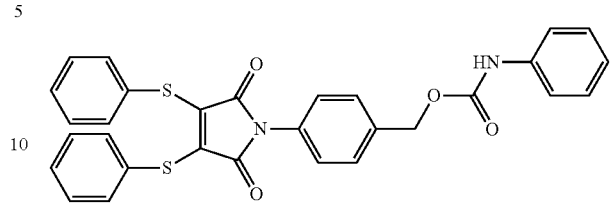

To a solution of N-hydroxymethylphenyl-diphenylthiolmaleimide 10 (105 mg, 0.251 mmol) in DCM (12 mL) were added phenylisocyanate (0.028 mL, 0.263 mmol) and NEt$_3$ (0.073 mL, 0.526 mmol) and the mixture was stirred for 2 days at room temperature and then concentrated to dryness. The crude residue was purified by flash chromatography to afford the title compound as a yellow solid (107 mg, 0.198 mmol, 79%).

$R_f$ 0.48 (30% EtOAc/petroleum ether); m.p. 130-132° C.; $v_{max}$ (cm$^{-1}$) 3367, 2928, 1714, 1600, 1535, 1444, 1384, 1218; $\delta_H$ (CDCl$_3$, 600 MHz) 7.45 (2H, d, J=8.4 Hz, ArHCH$_2$O), 7.37-7.33 (4H, m, ArHCH$_2$O and ArHNH), 7.32-7.21 (12H, m, ArHNH and ArHS), 7.07 (1H, t, J=7.4 Hz, ArHNH), 6.54 (1H, br s, NH), 5.18 (2H, s, CH$_2$OCONH); $\delta_C$ (CDCl$_3$, 150 MHz) 165.7, 153.2, 137.7, 135.8, 132.3, 131.5, 129.5, 129.2, 129.2, 129.0, 128.8, 128.7, 126.0, 121.5, 118.8, 66.4; Mass calculated for $C_{30}H_{22}N_2O_4NaS_2$: 561.0919, observed: 561.0939.

p-(diethylthiolmaleimide)-benzyl butylcarbamate (12)

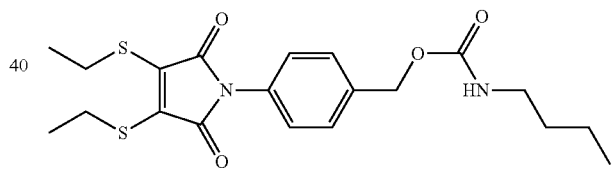

A solution of p-(diethylthiolmaleimide)-benzyl 4-nitrophenyl carbonate 9 (44.3 mg, 0.091 mmol) and butylamine (0.01 mL, 0.100 mmol) in NMP (4 mL) at room temperature were treated with Et$_3$N (0.014 mL, 0.100 mmol). The mixture was allowed to stand in the dark for 2 days and then it was diluted with EtOAc and was washed with H$_2$O and brine, dried over MgSO$_4$, filtered and concentrated in vacuo. The crude residue was purified by column chromatography to give the title product as yellow oil (17.6 mg, 0.042 mmol, 46%).

$R_f$ 0.53 (30% EtOAc/petroleum ether); $v_{max}$ (cm$^{-1}$) 3350, 2960, 2930, 2871, 1709, 1518, 1380, 1247; $\delta_H$ (CDCl$_3$, 600 MHz) 7.44 (2H, d, J=8.2 Hz, ArH), 7.32 (2H, d, J=8.2 Hz, ArH), 5.10 (2H, s, CH$_2$OCONH), 4.74 (1H, br s, NH), 3.36 (4H, q, J=7.4 Hz, CH$_3$CH$_2$S), 3.19 (2H, q, J=6.7 Hz, CH$_2$NH), 1.51-1.46 (2H, m, CH$_3$CH$_2$CH$_2$CH$_2$NH), 1.37 (6H, t, J=7.4 Hz, CH$_3$CH$_2$S), 1.36-1.30 (2H, m, CH$_3$CH$_2$CH$_2$CH$_2$NH), 0.92 (3H, t, J=7.3 Hz, CH$_3$CH$_2$CH$_2$CH$_2$NH); $\delta_C$ (CDCl$_3$, 150 MHz) 165.4, 156.3, 136.5, 135.8, 131.3, 128.9, 126.2, 66.9, 40.9, 32.1, 26.4, 20.0, 15.8, 13.9; Mass calculated for $C_{20}H_{26}N_2O_4NaS_2$: 445.1232, observed: 445.1232.

p-(diphenylthiolmaleimide)-benzyl 4-nitrophenyl carbonate (13)

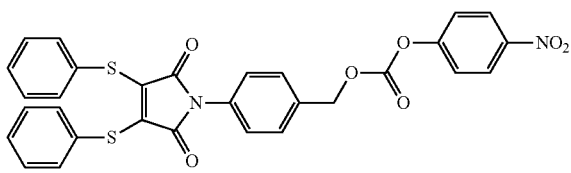 [SMILES: O=C(OCc1ccc(N2C(=O)C(Sc3ccccc3)=C(Sc3ccccc3)C2=O)cc1)Oc1ccc([N+](=O)[O-])cc1]

To a solution of N-hydroxymethylphenyl-diphenylthiol-maleimide 10 (30 mg, 0.071 mmol) in DCM (2 mL) were added 4-nitrophenylchloroformate (17 mg, 0.085 mmol) and pyridine (0.007 mL, 0.085 mmol) and the mixture was stirred for 24 h at room temperature. Then DCM (10 mL) and 10% aqueous citric acid (10 mL) were added and the organic layer was washed with H$_2$O and brine, dried over MgSO$_4$, filtered and concentrated. The crude residue was purified by flash chromatography to afford the title compound (30 mg, 0.051 mmol, 72%).

R$_f$ 0.63 (50% EtOAc/petroleum ether); ν$_{max}$ (cm$^{-1}$) 3080, 1767, 1714, 1594, 1520, 1382, 1339, 1260, 1213; δ$_H$ (CDCl$_3$, 600 MHz) 8.27 (2H, d, J=8.3 Hz, ArHNO$_2$), 7.49 (2H, d, J=8.3 Hz, ArHNO$_2$), 7.40 (2H, d, J=8.3 Hz, ArHCH$_2$O), 7.37 (2H, d, J=8.3 Hz, ArHCH$_2$O), 7.33-7.26 (10H, m, ArHS) 5.28 (2H, s, CH$_2$OCO$_2$); δ$_C$ (CDCl$_3$, 150 MHz) 165.6, 155.5, 152.5, 147.6, 135.9, 133.8, 132.3, 132.1, 129.5, 129.2, 128.8, 128.7, 126.2, 125.5, 121.9, 70.3.

p-(diphenylthiolmaleimide)-benzyl DOXcarbamate (14)

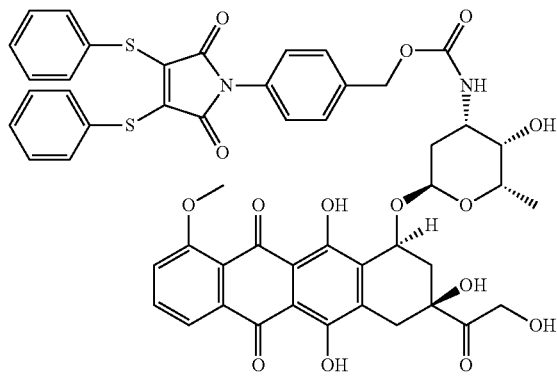 [SMILES: COc1cccc2c1C(=O)c1c(O)c3c(c(O)c1C2=O)C[C@@](O)(C(=O)CO)C[C@@H]3O[C@H]1C[C@H](NC(=O)OCc2ccc(N3C(=O)C(Sc4ccccc4)=C(Sc4ccccc4)C3=O)cc2)[C@H](O)[C@H](C)O1]

A solution of p-(diphenylthiolmaleimide)-benzyl 4-nitrophenyl carbonate 13 (9.8 mg, 0.017 mmol) and DOX.HCl (10 mg, 0.018 mmol) in NMP (0.3 mL) at room temperature were treated with Et$_3$N (0.0025 mL, 0.018 mmol). The mixture was allowed to stand in the dark for 3 days and then it was diluted with 10% i-propanol/EtOAc and was washed with H$_2$O and brine, dried over MgSO$_4$, filtered and concentrated in vacuo. The crude residue was purified by column chromatography to give the title product as yellow oil (16.4 mg, 0.0166 mmol, 99%).

R$_f$ 0.35 (5% MeOH/DCM); [α]$_D^{20}$=+91.3 (c 1.1, CHCl$_3$); ν$_{max}$ (cm$^{-1}$) 3481, 3080, 1716, 1580, 1517, 1383, 1286, 1073, 987; δ$_H$(CDCl$_3$, 600 MHz) 13.96 (1H, s, DOX), 13.22 (1H, s, DOX), 8.02 (1H, d, J=8.2 Hz, DOX), 7.77 (1H, d, J=8.2 Hz), 7.38 (2H, d, J=8.2 Hz, DOX), 7.34 (2H, d, J=8.2 Hz, ArHCH$_2$), 7.31-7.22 (12H, m, ArHCH$_2$ (2) and ArHS (10)), 5.49 (1H, br s, DOX), 5.27 (1H, br s, DOX), 5.18 (1H, d, J=8.6 Hz, DOX), 5.03-4.98 (2H, m, DOX), 4.75 (2H, s, CH$_2$O), 4.14-4.10 (1H, m, DOX), 4.07 (3H, s, DOX), 3.86-3.82 (1H, m, DOX), 3.65 (1H, s, DOX), 3.25 (1H, d, J=18.7 Hz, DOX), 2.98 (1H, d, J=18.7 Hz), 2.32 (1H, d, J=14.6 Hz, DOX), 2.16 (1H, dd, J=14.6 and 4.0 Hz, DOX), 1.86 (1H, dd, J=13.4 and 4.9 Hz, DOX), 1.79-1.76 (1H, m, DOX), 1.27 (3H, d, J=6.6 Hz, DOX); δ$_C$ (CDCl$_3$, 150 MHz) 214.0, 187.2, 186.8, 165.7, 161.1, 156.3, 155.7, 155.5, 136.1, 135.9, 135.7, 135.6, 133.7, 132.2, 131.2, 129.2, 129.2, 128.9, 128.9, 128.7, 125.9, 120.9, 120.0, 118.6, 111.7, 111.5, 100.8, 76.7, 69.7, 69.6, 67.4, 66.1, 65.7, 56.8, 47.1, 35.7, 34.1, 30.2, 17.0; Mass calculated for C$_{51}$H$_{44}$N$_2$O$_{15}$NaS$_2$: 1011.2081, observed: 1011.2122.

Example 1: Synthesis and Acid-Catalysed Cleavage of an Antibody Fragment-Cytotoxin Conjugate Attached Via a Thiomaleamic Acid Linker General Methods LCMS was performed on protein samples using a Waters Acquity UPLC connected to Waters Acquity Single Quad Detector [column, Acquity UPLC BEH C18 1.7 µm 2.1×50 mm; wavelength, 254 nm; mobile phase, 95:5 water (0.1% formic acid): MeCN (0.1% formic acid), gradient over 4 min to 5:95 water (0.1% formic acid): MeCN (0.1% formic acid); flow rate, 0.6 mL/min; MS mode, ES+/−; scan range, m/z=95-2000; scan time, 0.25 s]. Data were obtained in continuum mode. Sample volume was 30 µl and injection volumes were 3-9 µl with partial loop fill. The electron spray source of the MS was operated with a capillary voltage of 3.5 kV and a cone voltage of 20-200 V. Nitrogen was used as the nebulizer and desolvation gas at a total flow of 600 L/h. Total mass spectra were reconstructed from the ion series using the MaxEnt 1 algorithm pre-installed on MassLynx software.

Relative quantification of MS data was carried out by normalisation of all identifiable peptide or protein signals (starting material, product, side and degradation products) to 100% according to their unmodified signal strength (relative ion count).

Absorbance measurements were carried out on a Carry Bio 100 (Varian) UV/Vis spectrophotometer equipped with a temperature-controlled 12× sample holder in quartz cuvettes (1 cm path length, volume 75 µl) at 25° C. Samples were baseline corrected and slits set to 5 nm. Protein solutions were scanned from 450-250 nm and concentration calculated using either the published or calculated (based on the amino acid sequence via the ProtParam tool of the ExPASy data base; http://expasy.org/sprot/) molar extinction coefficients with Lambert Beers law.

Materials

Anti-CEA is single chain antibody fragment directed against the most N-terminal (extracellular) Ig domain of human CEA which it binds with low nM affinity. The original scFv is a mouse antibody isolated from a phage display and is produced in large quantities in bacteria (E. coli). The construct used in this work (internal name shMFELL2Cys) is a humanised version (28 amino acid substitutions) comprising the variable domain of a heavy and a light chain respectively which are connected by a peptide linker and has a MW of 26,742 Da (246 amino acids). A His$_6$-tag has been added to the C-terminus to facilitate purification and an artificial disulfide bond was introduced opposite to the antigen binding site (G44C and A239C) to stabilise the protein. A crystal structure of the parental antibody is available (PDB code: 1QOK). The material supplied by Dr Berend Tolner (UCL Cancer Institute) was to 90% pure as estimated from SDS-PAGE analysis.

Preparation of Anti-CEA Solutions

Anti-CEA was supplied in PBS (pH 7.4) in varying concentrations and stored in aliquots at −20° C. The antibody fragment was diluted in PBS (pH 7.4) and DMF (final amount 20% v/v) to yield a concentration of 70.0 µM (1.87 mg/ml) prior to experimentation. An extinction coefficient of $\varepsilon_{280}=48735$ $M^{-1}$ $cm^{-1}$ was used to calculate protein concentrations.

Preparation of Anti-CEA Linked Via Maleimide to Benzyl Phenylcarbamate

To anti-CEA were added 20 equiv of p-(diphenylthiolmaleimide)-benzyl phenylcarbamate 11 (in DMF) followed by 15 equiv of benzeneselenol (in DMF). The reaction was maintained at ambient temperature for 20 min, after which another portion of benzeneselenol was added. The sample was analysed by LCMS after 45 min and showed 99% conversion to anti-CEA linked via maleimide to benzyl phenylcarbamate (required mass 27,060 Da).

Hydrolysis Study of Anti-CEA Linked Via Maleimide to Benzyl Phenylcarbamate

Anti-CEA linked via maleimide to benzyl phenylcarbamate was prepared as described and the excess of the maleimide compound was removed by purification on PD MiniTrap G-25 desalting columns (GE Healthcare) following manufacturers' instructions. The concentration of the protein solution was determined by UV/Vis spectroscopy.

The modified antibody (in PBS, pH 7.4) was incubated at ambient temperature or at 37° C. for 6 h and aliquots were withdrawn at 1, 2, 4 and 6 h and subjected to LCMS to analyse for hydrolysis of the maleimide bridge to produce the desired thiomaleamic acid construct (required mass 27,078 Da). Full hydrolysis was observed at 37° C. after 6 h, as shown in FIG. 1.

Stability of Anti-CEA Linked Via Maleimide to Benzyl Phenylcarbamate

Anti-CEA linked via maleimide to benzyl phenylcarbamate was prepared, purified and the concentration determined as described.

Anti-CEA linked via maleimide to benzyl phenylcarbamate (in PBS, pH 7.4) was incubated at 37° C. for 5 d. Aliquots were removed every 24 h and analysed for degradation products of the maleimide compound by LCMS. No prominent mass ions corresponding to potential fragmentation of the linker were observed.

Disassembly of the Linker in Acidic pH

Anti-CEA linked via maleimide to benzyl phenylcarbamate was prepared, purified and the concentration determined as described. The material was incubated for 20 h at 37° C. and complete hydrolysis confirmed by LCMS. The resulting thiomaleamic acid construct was then transferred into a pH 4.0 or pH 5.0 buffer (50 mM citric acid, 150 mM sodium chloride) on PD MiniTrap G-25 desalting columns and the eluate concentrated with ultrafiltration columns (5 kDa MWCO, Sartorius).

The samples were incubated at 37° C. and aliquots withdrawn and analysed by LCMS after 0.5, 2, 5, 24 and 48 h. Disassembly of the linker and formation of the antibody fragment with maleic acid inserted into the disulfide bond (required mass 26,854 Da) was observed with great efficiency (>90% conversion in both cases after 48 h).

Preparation of an Anti-CEA-Benzyl DOXcarbamate Conjugate

Anti-CEA was prepared in PBS, pH 7.4, 10% DMF (v/v), 20% MeCN (v/v) at the concentration described above. To the antibody fragment were added 5 equiv of p-(diphenylthiolmaleimide)-benzyl DOXcarbamate 14 (in DMF) followed by 25 equiv of benzeneselenol (in DMF). Full conversion to an anti-CEA-DOX conjugate (required mass 27,510 Da) was observed by LCMS after 30 min at ambient temperature.

Release of Doxorubicin in Acidic pH

The anti-CEA-DOX conjugate was prepared as described and purified on PD MiniTrap G-25 desalting columns. The material was incubated for 20 h at 37° C. and complete hydrolysis to the desired thiomaleamic acid construct confirmed by LCMS (required mass 27,528 Da). The buffer-pH (PBS, pH 7.4) was then changed to pH 4.5 (50 mM citric acid, 150 mM sodium chloride) via PD MiniTrap G-25 desalting columns and the eluate concentrated with ultrafiltration columns (5 kDa MWCO).

The thiomaleamic acid construct was incubated at 37° C. and aliquots analysed after 0.5, 2, 5, 24 and 48 h by LCMS. Doxorubicin was released upon linker disassembly and anti-CEA-maleic acid formed in >80% yield (after 48 h). The appearance of free doxorubicin could be monitored in addition to the anti-CEA maleic acid.

Example 2: Exemplification of Maleamate Cleavage on an Fab Antibody Fragment

Preparation of Trastuzumab-Fab Fragment

Immobilized pepsin (0.15 mL) was washed 4× with buffer (20 mM sodium acetate, pH 3.1) and Trastuzumab (0.5 mL, 6.41 mg/mL in the same buffer) was added. The mixture was incubated for 5 h at 37° C. under agitation (1,100 rpm). The resin was separated from the digest using a filter column, and washed 3× with digest buffer (50 mM sodium phosphate, 1 mM EDTA, 150 mM NaCl, pH 6.8). The digest was combined with the washes and the volume adjusted to 0.5 mL (Trastuzumab-Fab2, observed mass by LCMS: 97,303 Da).

Immobilised papain (1 mL, 0.25 mg/mL) was activated with 10 mM DTT (in digest buffer) under an argon atmosphere and constant agitation (1,100 rpm) for 1 h at 25° C. in the dark. The resin was washed 4× with digest buffer (without DTT) and the 0.5 mL of Trastuzumab-Fab2 solution was added. The mixture was incubated for 16 h at 37° C. under constant agitation (1,100 rpm) in the dark. The resin was separated from the digest using a filter column, washed 3× with PBS (pH 7.0) and the digest combined with the washes. The buffer was exchanged completely for PBS using ultrafiltration columns (5 kDa MWCO) and the volume adjusted to 0.4 mL.

The digest was analysed by SDS-PAGE, LCMS (observed mass 47,650 Da) and the concentration of the FAb fragment was determined by UV/VIS using a molecular extinction coefficient of $_{280}=68,590$ $M^{-1}$ $cm^{-1}$. Yield [Fab]: 400 µl of a 3.33 mg/mL solution (64%).

Preparation of the Trastuzumab-Fab-Dox Conjugate 1

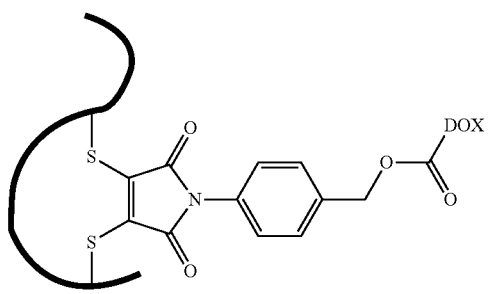

To a solution of Trastuzumab-Fab (50 µL, 1.72 mg/mL) in borate buffer (25 mM sodium borate, 25 mM NaCl, 1 mM EDTA, pH 8.0), was added TCEP (15 µL, 0.103 mg/mL, 3 equiv) and after incubation at 90 min at 37° C., MeCN (13 µL, 20% v/v), DMF (6.5 µL, 10% v/v) and p-(diphenylthiolmaleimide)-benzyl phenylcarbamate in DMF (1.15 µL, 7.82 mg/mL, 5 equiv) were added. The reaction was maintained at 37° C. for 1 h and analysed by LCMS, showing quantitative conversion to the desired Trastuzumab-Fab-DOX conjugate (observed mass 48,429 Da).

Preparation of Trastuzumab-Fab-DOX Conjugate 2

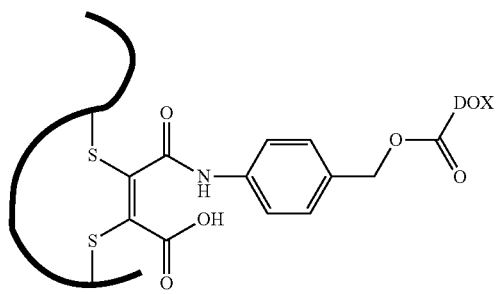

The Trastuzumab-Fab-DOX conjugate 1 was prepared as described above and the buffer was exchanged for PBS (pH 7.4). The sample was incubated at 37° C. for 20 h and complete hydrolysis to yield conjugate 2 confirmed by LCMS (observed mass 48,433 Da).

Trastuzumab-Fab-DOX Conjugate 2 is Stable at Physiological Temperature and pH

Trastuzumab-Fab-DOX conjugate 2 was incubated for 3 d at 37° C. No degradation products were observed by LCMS.

DOX is Released from Trastuzumab-Fab-DOX Conjugate 2 at Lysosomal pH

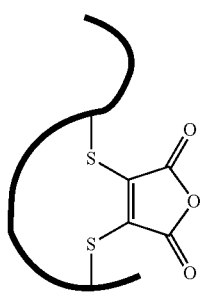

Trastuzumab-Fab-DOX conjugate 2 was prepared as described. The pH was then changed by ultrafiltration (10 kDa MWCO, Sartorius) to pH 4.5 (50 mM citric acid, 150 mM sodium chloride). The antibody conjugate was incubated at 37° C. and aliquots were analysed after 2, 6, 24, 48 and 72 h by LCMS. Doxorubicin was released upon linker disassembly and Trastuzumab-Fab-maleic anhydride formed (mass 47740 Da, quantitative conversion over 72 h).

Figure 2:
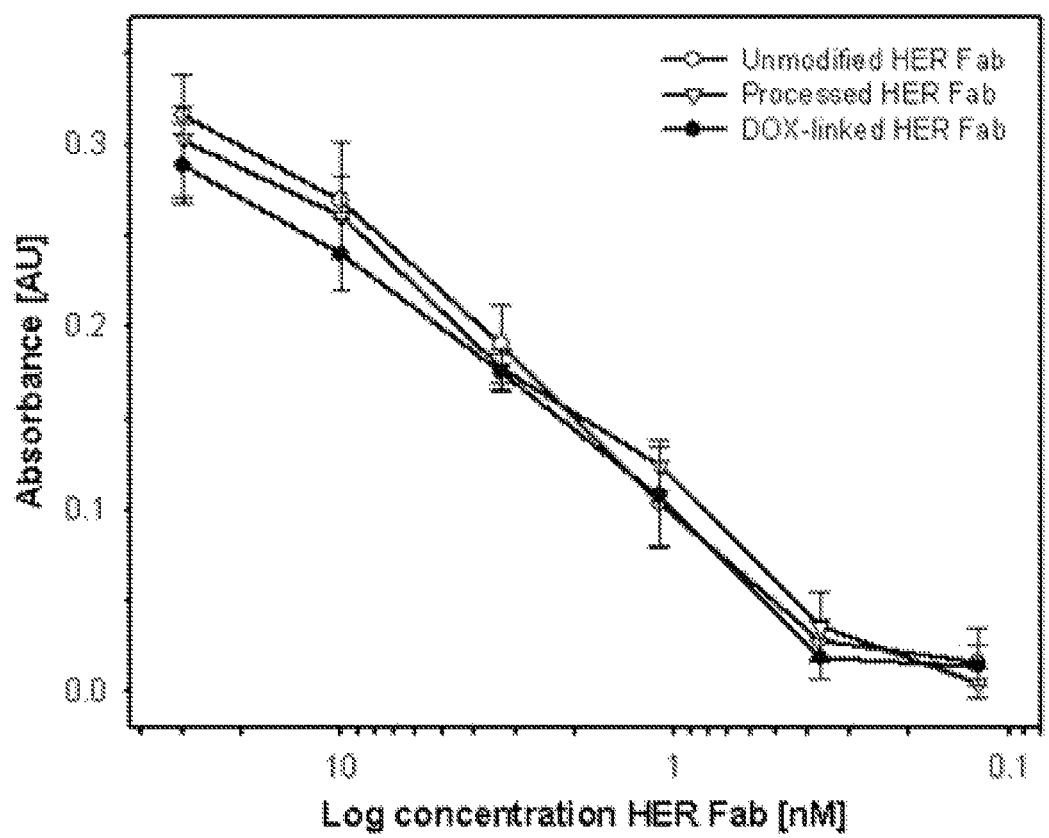
FIG. 2 depicts the results of ELISA analysis of the retention of binding of Trastuzumab-Fab to HER2 after conjugation according to the procedure described in Example 2. The x-axis represents the log of the concentration of HER Fab in nM and the y-axis represents absorbance [AU]. Filled circles correspond to the DOX-linked HER Fab of Example 2, open circles correspond to an unmodified HER Fab (control) and open triangles correspond to a 'processed' HER Fab as described in Example 2 (control).

Binding of Trastuzumab-Fab to HER2 is Maintained after Conjugation of Linker-DOX The Trastuzumab-Fab-DOX conjugate was prepared and purified as described. A 'processed Trastuzumab-Fab sample' was prepared as a control by subjecting Trastuzumab-Fab to all conjugation conditions other than reducing agent. The concentration of the material was measured using a Bradford standard curve (Quick Start Bardford Kit, Bio-Rad). ELISA plates were coated with soluble HER2 diluted to a final concentration of 0.25 µg/ml in PBS, incubated for 2 h at ambient temperature, washed and blocked over night at 4° C. with a 1% BSA solution (in PBS, Sigma-Aldrich). Plates were washed and the Trastuzumab-Fab and its analogues were added after dilution to the indicated concentrations (typically 30.0, 10.0, 3.33, 1.11, 0.37 and 0.12 nM) in PBS. The assay was incubated at ambient temperature for 2 h, washed and the primary antibody (anti-human IgG, Fab-specific-HRP, 1:5,000 in PBS) added. The plates were washed after 1 h at ambient temperature and freshly prepared substrate solution (one tablet of o-phenylenediamine in 25 ml 50 µM phosphate citrate buffer, Sigma-Aldrich) was added to each well. When a strong orange colour had developed the reaction was stopped by addition of 4 M HCl and the plates read at a wavelength of 490 nm Controls were included in every ELISA, in which PBS had been added to some of the wells instead of HER2 or instead of the antibody fragment. The results are shown in FIG. 2. Each sample was tested in triplicate, and errors are shown as the standard deviation of the average.

Example 3: Exemplification of Maleamate Cleavage on an a Full Antibody

Preparation of Full Trastuzumab-DOX Conjugate

To full trastuzumab (15 µM, 2.2 mg/ml) in borate buffer (25 mM sodium borate, 25 mM NaCl, 1 mM EDTA, pH 8.0, 15% DMF v/v) were added 15 equiv p-(diphenylthiolmaleimide)-benzyl phenylcarbamate (in DMF) followed by 10 equiv TCEP (in borate buffer). The reaction was maintained for 2 h at 37° C. under mild agitation and stopped via the addition of 50 eq maleimide (in DMF). The excess of reagents were removed by ultrafiltration (10 kDa MWCO) and the buffer exchanged for PBS (pH 7.4). The drug-to-antibody ratio (DAR) was measured via UV/Vis an calculated with the formula $$DAR = \frac{\frac{OD_{495}}{8030\ M^{-1}cm^{-1}}}{\frac{(OD_{280} - OD_{495} \times 0.724)}{210000\ M^{-1}cm^{-1}}}, \text{to be } 3.1 \pm 0.2.$$

DOX is Released from Full Trastuzumab-DOX Conjugate at Lysosomal pH

Figure 3:
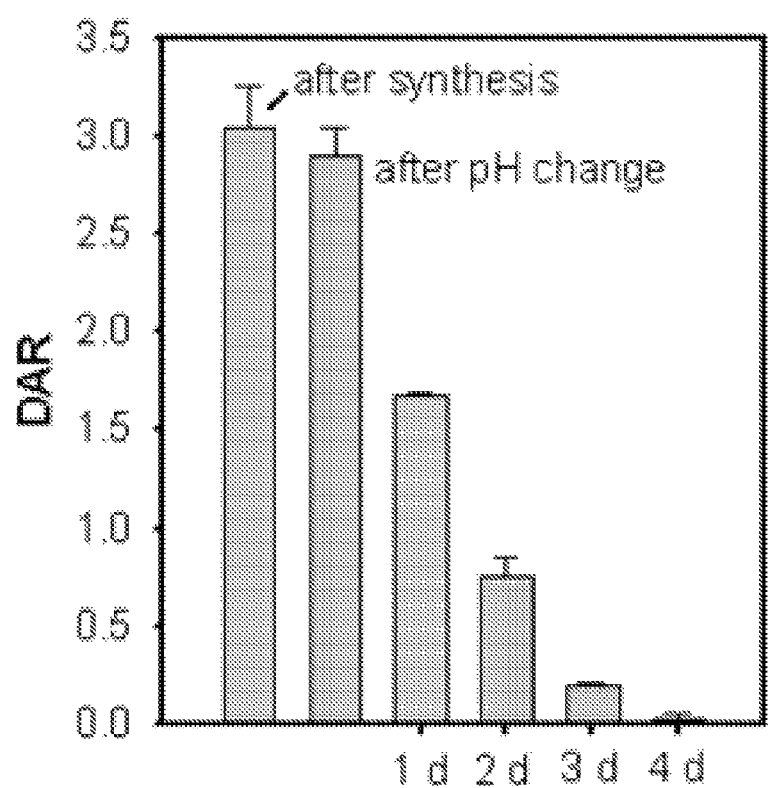
FIG. 3 depicts DAR (drug-to antibody ratio) of the full Trastuzumab-DOX conjugate of Example 3, as measured by UV/Vis analysis, as a function of time under lysosomal pH as described in Example 3. The y-axis represents DAR. The blocks along the x-axis, from left to right, represent the following test results: (i) after synthesis; (ii) after pH change; (iii) one day after pH change; (iv) two days after pH change; (v) three days after pH change; and (vi) four days after pH change.

The full Trastuzumab-DOX conjugate was synthesised and purified as described. The sample was incubated for 16 h at 37° C. to facilitate hydrolysis of the maleimide bridges. The DAR was measured and the buffer exchanged for a pH 4.5 citric acid buffer (50 mM citric acid, 150 mM sodium chloride) by ultrafiltration (10 kDa MWCO). Aliquots were withdrawn during the following incubation at 37° C. after 24, 48, 72 and 96 h and extensively washed in ultrafiltration columns (10 kDa MWCO) with sterile $H_2O$ at 4° C. to remove any released doxorubicin. The DAR of these samples was then immediately determined by UV/Vis as described above. The results are shown in FIG. 3.

The invention claimed is:

1. A compound of formula (Ia), (Ib) or (Ic)

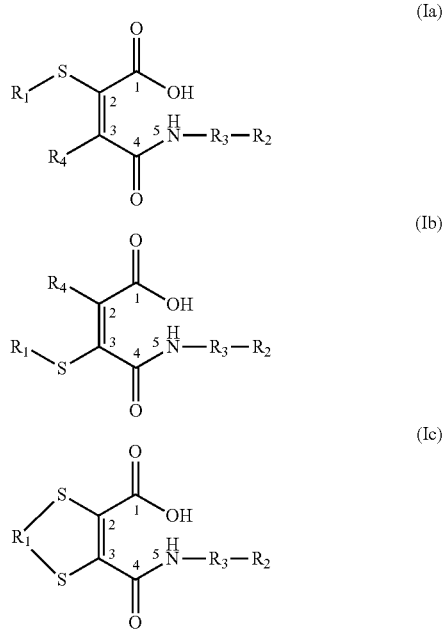

wherein:
$R_1$ is an antibody or antibody fragment, wherein said antibody or antibody fragment is capable of binding to an antigen;
$R_2$ is a therapeutically active agent;
$R_3$ is a linker moiety or a bond; and
$R_4$ is a hydrogen or halogen atom or a $C_{1-20}$ alkyl, $C_{2-20}$ alkenyl or $C_{2-20}$ alkynyl group, which group is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups are replaced by groups selected from —O—, —S—, —S—S—, —C(O)— and —N($C_{1-6}$ alkyl)- groups, wherein:
   (i) said arylene, heteroarylene, carbocyclylene and heterocyclylene groups are unsubstituted or substituted by one or more substituents selected from halogen atoms and $C_{1-6}$ alkyl, $C_{1-6}$ alkoxy, $C_{1-6}$ alkylthiol, —N($C_{1-6}$ alkyl)($C_{1-6}$ alkyl), nitro and sulfonic acid groups; and
   (ii) 0, 1 or 2 carbon atoms in said carbocyclylene and heterocyclylene groups are replaced by —C(O)— groups;
$R_1$ being linked to the 2-position of the moiety of formula (Ia) via a first sulfur atom attached to the 2-position of the moiety of formula (Ia); $R_1$ being linked to the 3-position of the moiety of formula (Ib) via a first sulfur atom attached to the 3-position of the moiety of formula (Ib); and $R_1$ being linked to the 2-position of the moiety of formula (Ic) via a first sulfur atom attached to the 2-position of the moiety of formula (Ic) and $R_1$ being linked to the 3-position of the moiety of formula (Ic) via a second sulfur atom attached to the 3-position of the moiety of formula (Ic).

2. A compound according to claim 1, wherein said first sulfur atom is the sulfur atom of a first cysteine residue in $R_1$.

3. A compound according to claim 2, which is a compound of formula (Ic) and wherein said second sulfur atom is the sulfur atom of a second cysteine residue in $R_1$.

4. A compound according to claim 3, wherein said first sulfur atom and said second sulfur atom are attached to one another via a disulfide bridge —S—S— when the protein or peptide is in isolated form.

5. A compound according to claim 1, wherein $R_1$ is capable of specific binding to a target cell.

6. A compound according to claim 5, wherein $R_1$ is capable of specific binding to a cancer cell.

7. A compound according to claim 1, wherein said antibody or antibody fragment is capable of specific binding to an antigen selected from MY9, B4, EpCAM, CD2, CD3, CD4, CD5, CD6, CD11, CD19, CD20, CD22, CD25, CD26, CD30, CD33, CD37, CD38, CD40, CD44, CD56, CD64, CD70, CD74, CD79, CD105, CD138, CD205, CD227, EphA receptors, EphB receptors, EGFR, EGFRvIII, HER2, HER3, BCMA, PSMA, Lewis Y, mesothelin, cripto, alpha (v)beta3, alpha(v)beta5, alpha(v) beta6 integrin, C242, CA125, GPNMB, ED-B, TMEFF2, FAP, TAG-72, GD2, CAIX and 5T4.

8. A compound according to claim 1, wherein $R_2$ has greater therapeutic activity following hydrolysis of the compound of formula (Ia), (Ib) or (Ic) than when it forms part of the compound of formula (Ia), (Ib) or (Icy.

9. A compound according to claim 1, wherein $R_2$ is a cytotoxic agent.

10. A compound according to claim 1, wherein $R_2$ is selected from anthracyclines, auristatins, maytansinoids, calicheamicins, taxanes, benzodiazepines and duocarmycins.

11. A compound according to claim 1, wherein $R_1$ is an antibody or antibody fragment that is capable of specific binding to a cancer cell and $R_2$ is a cytotoxic agent.

12. A compound according to claim 1, wherein the compound of formula (Ia), (Ib) or (Ic) is capable of hydrolyzing at a pH of from 4 to 5 to release a fragment of the formula $H_2N$—$R_3$—$R_2$.

13. A compound according to claim 1, wherein $R_3$ is a linker moiety that is capable of hydrolyzing to release the therapeutically active agent.

14. A compound according to claim 1, wherein $R_3$ is a linker moiety that is a $C_{1-20}$ alkylene group, a $C_{2-20}$ alkenylene group or a $C_{2-20}$ alkynylene group, which is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups are replaced by groups selected from —O—, —S—, —S—S—, —C(O)—, —NH—, —N($C_{1-6}$ alkyl)-, —O—C(O)—, —O—C(O)—NH—, —NH—C(O)— and —NH—C(O)—O— groups, wherein:
   (i) said arylene, heteroarylene, carbocyclylene and heterocyclylene groups are unsubstituted or substituted by one or more substituents selected from halogen atoms and nitro, carboxyl, cyano, acyl, acylamino, carboxamide, sulfonamide, trifluoromethyl, phosphate, $C_{1-6}$ alkyl, $C_{6-10}$ aryl, 5- to 10-membered heteroaryl, $C_{3-7}$ carbocyclyl, 5- to 10-membered heterocyclyl, $—OR_x$, $—SR_x$, $—N(R_x)(R_y)$ and $—SO_2—R_x$ groups, wherein $R_x$ and $R_y$ are independently selected from hydrogen atoms and $C_{1-6}$ alkyl and $C_{6-10}$ aryl groups; and (ii) 0, 1 or 2 carbon atoms in said carbocyclylene and heterocyclylene groups are replaced by —C(O)— groups.

15. A compound according to claim 1, wherein $R_3$ is a linker moiety containing a phenylene group attached to the nitrogen atom at the 5-position in the compound of formula (Ia), (Ib) or (Ic), said phenylene group being unsubstituted or substituted by one or more substituents selected from halogen atoms and nitro, carboxyl, cyano, acyl, acylamino, carboxamide, sulfonamide, trifluoromethyl, phosphate, $C_{1-6}$ alkyl, $C_{6-10}$ aryl, 5- to 10-membered heteroaryl, $C_{3-7}$ carbocyclyl, 5- to 10-membered heterocyclyl, $—OR_x$, $—SR_x$, $—N(R_x)(R_y)$ and $—SO_2—R_x$ groups, wherein $R_x$ and $R_y$ are independently selected from hydrogen atoms and $C_{1-6}$ alkyl and $C_{6-10}$ aryl groups.

16. A compound according to claim 1, wherein $R_3$ is a linker moiety that, together with the group $R_2$, comprises a carbamate moiety of formula —O—C(O)—N(H)— or —N(H)—C(O)—O—.

17. A compound according to claim 1, wherein $R_3$ is a linker moiety of formula -[A]-[B]-[C]-, wherein:

[A] is a phenylene group that is unsubstituted or substituted by one or more substituents selected from halogen atoms and nitro, carboxyl, cyano, acyl, acylamino, carboxamide, sulfonamide, trifluoromethyl, phosphate, $C_{1-6}$ alkyl, $C_{6-10}$ aryl, 5- to 10-membered heteroaryl, $C_{3-7}$ carbocyclyl, 5- to 10-membered heterocyclyl, $—OR_x$, $—SR_x$, $—N(R_x)(R_y)$ and $—SO_2—R_x$ groups, wherein $R_x$ and $R_y$ are independently selected from hydrogen atoms and $C_{1-6}$ alkyl and $C_{6-10}$ aryl groups;

[B] is a bond or a $C_{1-6}$ alkyl group; and

[C] is a group of formula —O—C(O)—NH—, —O—C(O)—, —N(H)—C(O)—O— or —N(H)—C(O)—, such that the fragment —[C]—[$R_2$]— is attached to the fragment -[A]-[B]- via a carbamate moiety of formula —O—C(O)—N(H)— or —N(H)—C(O)—O—.

18. A compound according to claim 17, wherein $R_3$ is a linker moiety of formula

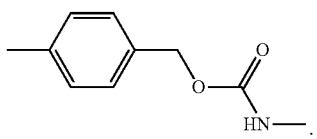

19. A compound according to claim 1, wherein $R_3$ is a bond and wherein the compound of formula (Ia), (Ib) or (Ic) is capable of hydrolyzing at a pH of from 4 to 5 to release a fragment of formula $H_2N—R_2$.

20. A compound according to claim 1, wherein the compound of formula (Ia), (Ib) or (Ic) is not capable of hydrolyzing to release the therapeutically active agent or a fragment of formula $H_2N—R_3—R_2$ or $H_2N—R_2$ at a pH of 7 or higher.

21. A compound according to claim 1, wherein $R_4$ is a hydrogen or halogen atom or an unsubstituted $C_{1-6}$ alkyl, $C_{2-6}$ alkenyl or $C_{2-6}$ alkynyl group, in which (a) 0 or 1 carbon atom is replaced by a group selected from phenylene, 5- to 6-membered heteroarylene, $C_{5-6}$ carbocyclylene and 5- to 6-membered heterocyclylene groups, wherein said phenylene, heteroarylene, carbocyclylene and heterocyclylene groups are unsubstituted or substituted by one or two substituents selected from halogen atoms and $C_{1-4}$ alkyl and $C_{1-4}$ alkoxy groups, and (b) 0, 1 or 2 —$CH_2$— groups are replaced by groups selected from —O—, —S— and —C(O)— groups.

22. A compound according to claim 21, wherein $R_4$ is a hydrogen atom or an unsubstituted $C_{1-6}$ alkyl group.

23. A pharmaceutical composition comprising:
(i) a compound of formula (Ia), (Ib) or (Ic)

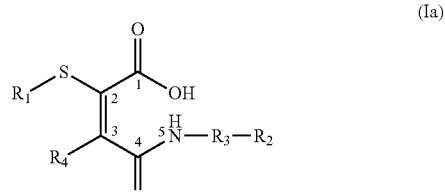

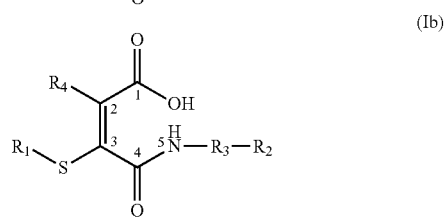

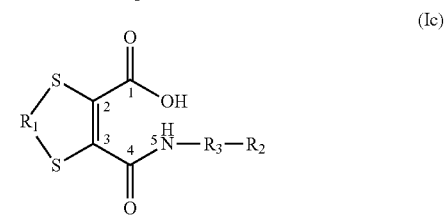

wherein:
$R_1$ is an antibody or antibody fragment, wherein said antibody or antibody fragment is capable of binding to an antigen;
$R_2$ is a therapeutically active agent;
$R_3$ is a linker moiety or a bond; and
$R_4$ is a hydrogen or halogen atom or a $C_{1-20}$ alkyl, $C_{2-20}$ alkenyl or $C_{2-20}$ alkynyl group, which group is unsubstituted or substituted by one or more substituents selected from halogen atoms and sulfonic acid groups, and in which (a) 0, 1 or 2 carbon atoms are replaced by groups selected from $C_{6-10}$ arylene, 5- to 10-membered heteroarylene, $C_{3-7}$ carbocyclylene and 5- to 10-membered heterocyclylene groups, and (b) 0, 1 or 2 —$CH_2$— groups are replaced by groups selected from —O—, —S—, —S—S—, —C(O)— and —N($C_{1-6}$ alkyl)- groups, wherein:

(i) said arylene, heteroarylene, carbocyclylene and heterocyclylene groups are unsubstituted or substituted by one or more substituents selected from halogen atoms and $C_{1-6}$ alkyl, $C_{1-6}$ alkoxy, $C_{1-6}$ alkylthiol, —N($C_{1-6}$ alkyl)($C_{1-6}$ alkyl), nitro and sulfonic acid groups; and (ii) 0, 1 or 2 carbon atoms in said carbocyclylene and heterocyclylene groups are replaced by —C(O)— groups;

$R_1$ being linked to the 2-position of the moiety of formula (Ia) via a first sulfur atom attached to the 2-position of the moiety of formula (Ia); $R_1$ being linked to the 3-position of the moiety of formula (Ib) via a first sulfur atom attached to the 3-position of the moiety of formula (Ib); and $R_1$ being linked to the 2-position of the moiety of formula (Ic) via a first sulfur atom attached to the 2-position of the moiety of formula (Ic) and $R_1$ being linked to the 3-position of the moiety of formula (Ic) via a second sulfur atom attached to the 3-position of the moiety of formula (Ic); and (ii) a pharmaceutically acceptable diluent or carrier.

24. A method of ameliorating or reducing the incidence of cancer in a subject, which method comprises the administration to the said subject of an effective amount of a compound of claim 1.

\* \* \* \* \*